US006265513B1

(12) United States Patent
Murray et al.

(10) Patent No.: US 6,265,513 B1
(45) Date of Patent: Jul. 24, 2001

(54) POLYOLEFIN

(75) Inventors: Rex E. Murray, Cross Lanes; Simon Mawson; Clark C. Williams, both of Charleston; James D. Schreck, Cross Lanes, all of WV (US)

(73) Assignee: Univation Technologies, LLC, Houston, TX (US)

( * ) Notice: Subject to any disclaimer, the term of this patent is extended or adjusted under 35 U.S.C. 154(b) by 0 days.

(21) Appl. No.: 09/216,163

(22) Filed: Dec. 18, 1998

Related U.S. Application Data
(60) Provisional application No. 60/051,581, filed on Jul. 2, 1997.

(51) Int. Cl.$^7$ ............................. C08F 10/02; C08F 10/06; C08F 10/08
(52) U.S. Cl. ..................... 526/352; 526/348; 526/348.6; 526/348.5
(58) Field of Search ................................. 526/160, 161, 526/170, 172, 348, 348.6, 352

(56) References Cited

U.S. PATENT DOCUMENTS

| | | | |
|---|---|---|---|
| 4,001,195 | 1/1977 | Wyatt | 526/348 |
| 4,508,842 | 4/1985 | Beran et al. | 502/112 |
| 4,752,597 | 6/1988 | Turner | 502/104 |
| 4,791,180 | 12/1988 | Turner | 526/160 |
| 4,808,561 | 2/1989 | Welborn, Jr. | 502/104 |
| 4,845,067 | 7/1989 | Kao et al. | 502/119 |
| 4,897,455 | 1/1990 | Welborn, Jr. | 526/129 |
| 4,914,253 | 4/1990 | Chang | 585/523 |
| 4,923,833 | 5/1990 | Kioka et al. | 502/9 |
| 4,999,327 | 3/1991 | Kao et al. | 502/119 |
| 5,008,228 | 4/1991 | Chang | 502/111 |
| 5,026,797 | 6/1991 | Takahashi | 526/124 |
| 5,077,255 | 12/1991 | Welborn, Jr. | 502/104 |
| 5,086,024 | 2/1992 | Crapo et al. | 502/117 |
| 5,086,025 | 2/1992 | Chang | 502/117 |
| 5,106,804 | 4/1992 | Bailly et al. | 502/108 |
| 5,122,491 | 6/1992 | Kioka et al. | 502/117 |
| 5,147,949 | 9/1992 | Chang | 526/129 |
| 5,155,079 | 10/1992 | Cribbs et al. | 502/113 |
| 5,206,199 | 4/1993 | Kioka et al. | 502/117 |
| 5,240,894 | 8/1993 | Burkhardt et al. | 502/108 |
| 5,270,407 | 12/1993 | Takeuchi et al. | 526/74 |
| 5,308,815 | 5/1994 | Sangokoya | 502/104 |
| 5,318,935 | 6/1994 | Canich et al. | 502/117 |
| 5,340,786 | 8/1994 | Tsutsui et al. | 502/117 |
| 5,405,922 | 4/1995 | DeChellis et al. | 526/68 |
| 5,420,220 | 5/1995 | Cheruvu et al. | 526/348 |
| 5,422,325 | 6/1995 | Jejelowo et al. | 502/104 |
| 5,434,116 | 7/1995 | Sone et al. | 502/103 |
| 5,466,649 | 11/1995 | Jejelowo | 502/120 |
| 5,473,028 | 12/1995 | Nowlin et al. | 526/114 |
| 5,516,737 | 5/1996 | Jejelowo | 502/104 |
| 5,516,861 | 5/1996 | Jejelowo | 526/126 |
| 5,539,076 * | 7/1996 | Nowlin et al. | 526/348.1 |
| 5,554,704 | 9/1996 | Burkhardt et al. | 526/153 |

(List continued on next page.)

FOREIGN PATENT DOCUMENTS

| | | |
|---|---|---|
| 0 619 325 A1 | 10/1994 | (EP) . |
| 0803520 B1 | 12/1998 | (EP) . |
| 1015054 | 12/1965 | (GB) . |
| 1126111 | 5/1989 | (JP) . |
| WO 96/23101 | 8/1996 | (WO) . |
| WO 96/33202 | 10/1996 | (WO) . |
| WO 97/02298 | 1/1997 | (WO) . |
| WO 98/49208 | 11/1998 | (WO) . |
| WO 99/01460 | 1/1999 | (WO) . |

OTHER PUBLICATIONS

Kempe et., Octahedral Group 4 Metal Complexes, Inorg. Chem. 1996, 35 6742–6745, 1996.*

Gibson, Vernon C. et al: "Synthesis and structural characterisation of aluminum imino–amide and pyridyl–amide complexes: bulky monoanionic N,N chelate ligands via methyl group transfer", Journal of Organometallic Chemistry, CH, Elsevier–Sequoia S.A. Lausanne, vol. 550, No. 1–2, Jan. 15, 1998, pp. 453–456.

*J. Organometallic Chem.*, Gibson et al., 550 (1998) 453–456.

*J. Organometallic Chem.*, Orrell et al., 555 (1998) 35–47.

*Inorg. Chem.*, Fuhrman et al., 1996, 35, 6742–6745.

*Primary Examiner*—David W. Wu
*Assistant Examiner*—Robert D. Harlan
(74) *Attorney, Agent, or Firm*—Jaimes Sher; Lisa Kimes Jones

(57) ABSTRACT

Polyolefin wherein
A) the melt indices of Fractions 1, 4 and 6 of the polyolefin do not vary by more than 20% relative to the mean of Fractions 1, 4 and 6; and/or B) the percent crystallinity of Fractions 1, 4 and 6 of the polyolefin do not vary by more than 6% relative to the mean of Fractions 1, 4 and 6; and/or C) the Mw/Mn of Fractions 1, 4 and 6 of the polyolefin do not vary by more than 20% relative to the mean of Fractions 1, 4 and 6; and/or D) Fraction 1 has an aspect ratio of 0.5–1.5, fraction 4 has an aspect ratio of 1.2 to 4, Fraction 6 has an aspect ratio of about 1.75 to 5 provided that the aspect ratios of the Fractions differ by at least 0.3;

E) and/or the Mw/Mn of the polyolefin is 10 or more;
and wherein Fractions 1, 4 and 6 are obtained by using the following sieves:

| Sieve size | Fraction Collected | Fraction Name |
|---|---|---|
| 10 mesh | >2000 μm | Fraction 1 |
| 18 mesh | 2000–1000 μm | Fraction 2 |
| 35 mesh | <1000–500 μm | Fraction 3 |
| 60 mesh | <500–250 μm | Fraction 4 |
| 120 mesh | <250–125 μm | Fraction 5 |
| pan | <125 μm | Fraction 6. |

49 Claims, 4 Drawing Sheets

U.S. PATENT DOCUMENTS

| | | | |
|---|---|---|---|
| 5,578,537 | 11/1996 | Herrmann et al. | 502/120 |
| 5,587,501 | 12/1996 | Winter et al. | 556/53 |
| 5,595,950 | 1/1997 | Sagar et al. | 502/104 |
| 5,599,885 | 2/1997 | Kawasaki et al. | 526/68 |
| 5,602,217 | 2/1997 | Jejelowo | 526/129 |
| 5,637,660 | 6/1997 | Nagy et al. | 526/160 |
| 5,684,098 | 11/1997 | Wang et al. | 526/133 |
| 5,714,427 | 2/1998 | Winter et al. | 502/117 |
| 5,723,705 | 3/1998 | Herrmann et al. | 585/9 |
| 5,726,115 | 3/1998 | Horton et al. | 502/152 |
| 5,753,578 | 5/1998 | Santi et al. | 502/114 |
| 5,814,574 | 9/1998 | McNally | 502/103 |
| 6,054,544 * | 4/2000 | Finlayson et al. | 526/348 |
| 6,117,959 * | 9/2000 | Ponasik, Jr. et al. | 526/172 |

* cited by examiner

POLYOLEFIN

STATEMENT OF RELATED APPLICATIONS

This application relates to U.S. Ser. No. 09/103,620 filed Jun. 23, 1998 claiming the benefit of provisional application No. 60/051,581, filed Jul. 2, 1997 and to concurrently filed U.S. patent applications Ser. Nos. 09/213,627, 09/215,706, and 09/216,215, all filed Dec. 18, 1998.

FIELD OF THE INVENTION

This invention relates to a polymer produced using an olefin polymerization catalysts based upon two transition metal compounds comprising bidentate ligands containing pyridine or quinoline moieties and mixtures thereof.

BACKGROUND OF THE INVENTION

The intense commercialization of metallocene polyolefin catalysts has led to widespread interest in the design of non-metallocene, homogeneous catalysts. This field is more than an academic curiosity as new, non-metallocene catalysts may provide an easier pathway to currently available products and may also provide product and process opportunities which are beyond the capability of metallocene catalysts. In addition, certain non-cyclopentadienyl ligands may be more economical due to the relative ease of synthesis of a variety of substituted analogs.

Thus there is a need in the art for new novel olefin polymerization catalysts and for the unique polymers they produce.

WO 96/23101, WO 97/02298, WO 96/33202 and Furhmann et al, *Inorg. Chem.* 35:6742–6745 (1996) all disclose nitrogen containing single site like catalyst systems.

SUMMARY OF THE INVENTION

This invention relates to a polymer produced by an olefin polymerization catalyst system comprising an activator and two or more transition metal catalysts based on bidentate ligands containing pyridine or quinoline moieties, such as those described in U.S. application Ser. No. 09/103,620 filed Jun. 23, 1998, which is herein incorporated by reference. This invention further relates to unique polyethylene resins, more preferably bimodal high density polyethylene resins produced by this invention.

DETAILED DESCRIPTION OF THE INVENTION

Figure 1:
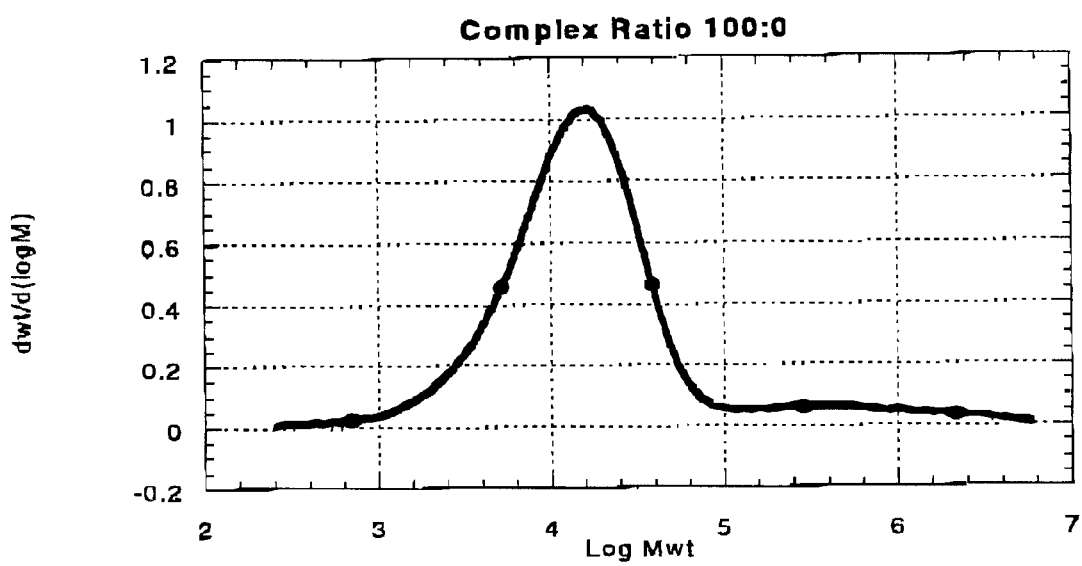
FIGS. 1–5 are plots of the log of weight average molecular weight versus the dwt/d(logM), a measure of molecular weight distribution for the runs in Table 1.
Figure 2:
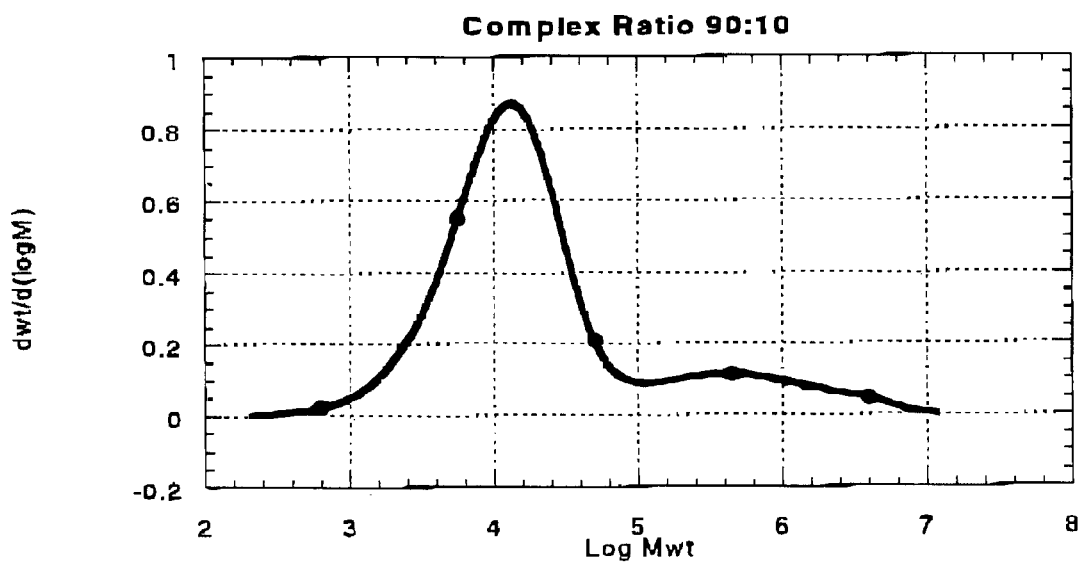
Figure 3:
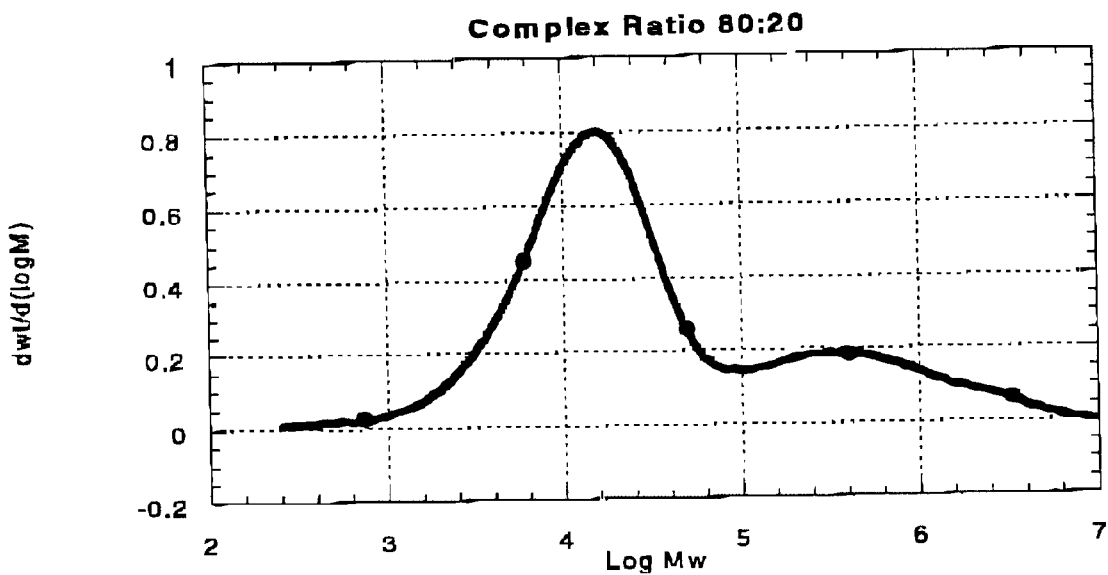
Figure 4:
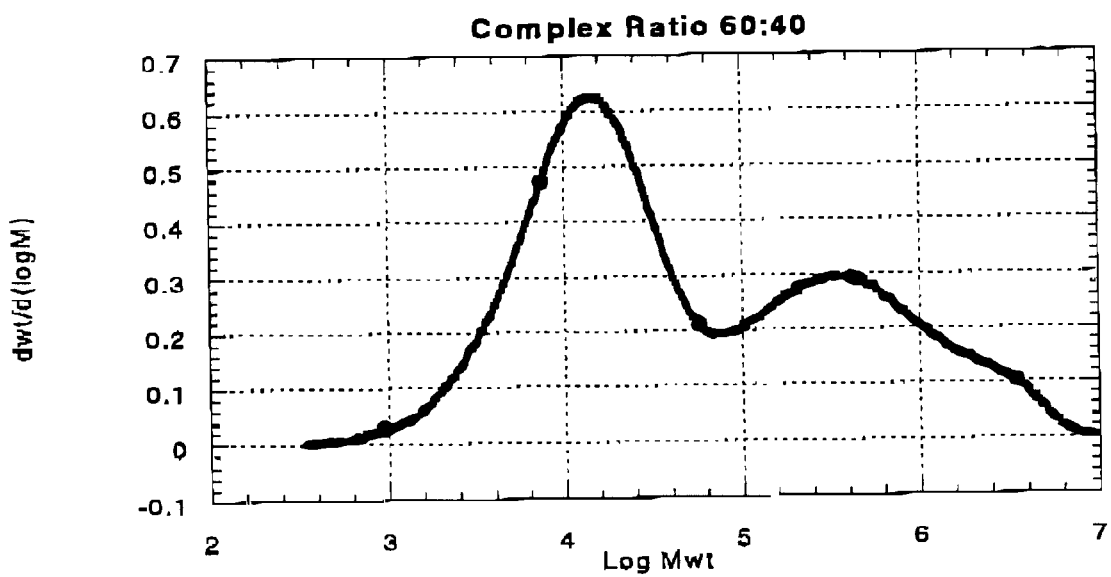
Figure 5:
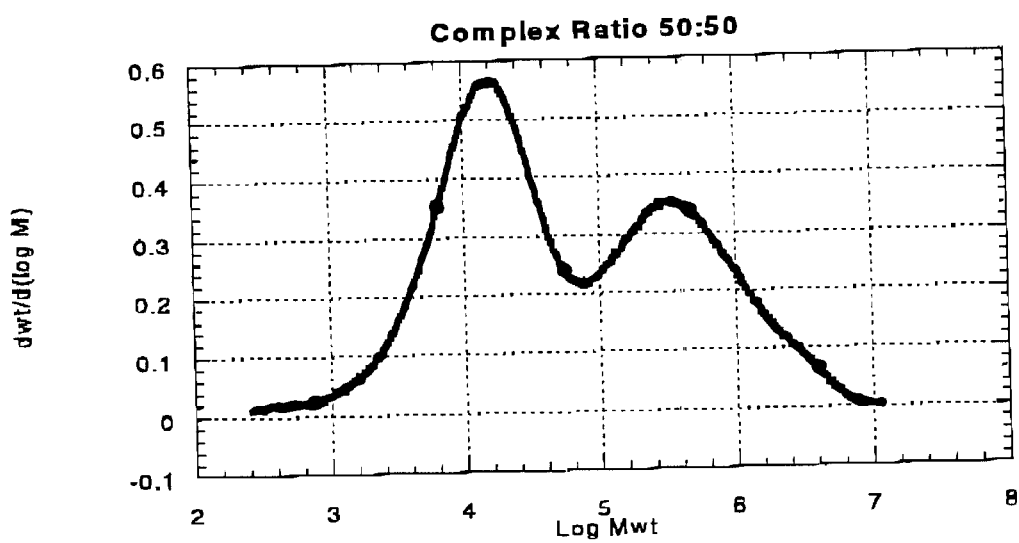

This invention relates to polyolefins produced by an olefin polymerization catalyst system comprising an activator and two or more transition metal catalysts based on bidentate ligands containing pyridine or quinoline moieties. The activator may be any known catalyst activator and in one embodiment is an alkyl aluminum, an alumoxane, a modified alumoxane, a polyalumoxane, a non-coordinating anion, a Lewis acid or a mixture thereof.

There are a variety of methods for preparing alumoxane and modified alumoxanes, non-limiting examples of which are described in U.S. Pat. Nos. 4,665,208, 4,952,540, 5,091, 352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253 and 5,731,451 and European publications EP-A-0 561 476, EP-B1-0 279 586 and EP-A-0 594-218, and PCT publication WO 94/10180, all of which are herein fully incorporated by reference.

Ionizing compounds (non-coordinating anions) may contain an active proton, or some other cation associated with but not coordinated to or only loosely coordinated to the remaining ion of the ionizing compound. Such compounds and the like are described in European publications EP-A-0 570 982, EP-A-0 520 732, EP-A-0 495 375, EP-A-0 426 637, EP-A-500 944, EP-A-0 277 003 and EP-A-0 277 004, and U.S. Pat. Nos. 5,153,157, 5,198,401, 5,066,741, 5,206, 197, 5,241,025, 5,387,568, 5,384,299 and 5,502,124 and U.S. patent application Ser. No 08/285,380, filed Aug. 3, 1994, all of which are herein fully incorporated by reference. Other activators include those described in PCT publication WO 98/07515 such as tris(2,2',2"-nonafluorobiphenyl) fluoroaluminate, which is fully incorporated herein by reference. Combinations of activators are also contemplated by the invention, for example, alumoxanes and ionizing activators in combinations, see for example, PCT publications WO 94/07928 and WO 95/14044 and U.S. Pat. Nos. 5,153, 157 and 5,453,410 all of which are herein fully incorporated by reference. Also, methods of activation such as using radiation and the like are also contemplated as activators for the purposes of this invention.

In one embodiment, the transition metal catalyst compound based on bidentate ligands containing pyridine or quinoline moieties is represented by the formula:

$$((Z)XA_t(YJ))_qMQ_n \qquad (I)$$

where M is a metal selected from Group 3 to 13 or lanthanide and actinide series of the Periodic Table of Elements; Q is bonded to M and each Q is a monovalent, divalent or trivalent anion; X and Y are bonded to M; X and Y are independently carbon or a heteroatom, provided that at least one of X and Y is a heteroatom, preferably both X and Y are heteroatoms; Y is contained in a heterocyclic ring J, where J comprises from 2 to 50 non-hydrogen atoms, preferably 2 to 30 carbon atoms; Z is bonded to X, where Z comprises 1 to 50 non-hydrogen atoms, preferably 1 to 50 carbon atoms or a silyl group, an alkyl silyl group such as a trialkyl silyl, preferably Z is a cyclic group containing 3 to 50 atoms, preferably 3 to 30 carbon atoms; t is 0 or 1; when t is 1, A is a bridging group joined to at least one of X, Y or J, preferably X and J; q is 1 or 2; n is the oxidation state of M minus q if Q is a monovalent anion, n is (the oxidation state of M–q)/2, if Q is a bivalent anion or n is 5 (the oxidation state of M–q)/3 if Q is a trivalent anion., typically n is an integer from 1 to 4 depending on the oxidation state of M. In one embodiment, if X is oxygen or sulfur then Z is optional. In another embodiment, if X is nitrogen or phosphorous then Z is present. In an embodiment, Z is preferably an aryl group, more preferably a substituted aryl group.

In another embodiment, these the transition metal catalyst compounds are represented by the formula:

$$((R'_mZ)XA(YJR''_p))_qMQ_n \qquad (II)$$

where M is a metal selected from Group 3 to 13 of the Periodic Table of Elements, preferably a Group 4 to 12 transition metal, more preferably a Group 4, 5 or 6 transition metal, even more preferably a Group 4 transition metal such as titanium, zirconium or hafnium, and most preferably zirconium;

Each Q is bonded to M and each Q is a monovalent, divalent or trivalent anion.

Preferably each Q is independently selected from the group consisting of halogens, hydrogen, alkyl, aryl, alkenyl, alkylaryl, arylalkyl, hydrocarboxy or phenoxy radicals having 1–20 carbon atoms. Each Q may also be amides, phosphides, sulfides, silylalkyls, diketonates, and carboxylates. Optionally, each Q may contain one or more heteroatoms, more preferably each Q is selected from the group consisting of halides, alkyl radicals and arylalkyl radicals. Most preferably, each Q is selected from the group consisting of arylalkyl radicals such as benzyl;

X and Y are both bound to M and are independently carbon or a heteroatom, provided that at least one of X and Y is a heteroatom, X and Y are preferably each heteroatoms, more preferably X and Y are independently selected from the group consisting of nitrogen, oxygen, sulfur and phosphorous, even more preferably nitrogen or phosphorous, and most preferably nitrogen;

Y is contained in a heterocyclic ring or ring system J. J contains from 2 to 30 carbon atoms, preferably from 2 to 7 carbon atoms, more preferably from 3 to 6 carbon atoms, and most preferably 5 carbon atoms. Optionally, the heterocyclic ring J containing Y, may contain additional heteroatoms. J may be substituted with R" groups that are independently selected from the group consisting of hydrogen or linear, branched, cyclic, alkyl radicals, or alkenyl, alkynyl, alkoxy, aryl or aryloxy radicals. Also, two or more R" groups may be joined to form a cyclic moiety such as an aliphatic or aromatic ring. Preferably R" is hydrogen or an aryl group, most preferably R" is hydrogen. When R" is an aryl group and Y is nitrogen, a quinoline group is formed. Optionally, an R" may be joined to A;

Z is a hydrocarbyl group bonded to X, preferably Z is a hydrocarbyl group of from 1 to 50 carbon atoms, preferably Z is a cyclic group having from 3 to 30 carbon atoms, preferably Z is a substituted or unsubstituted cyclic group containing from 3 to 30 carbon atoms, optionally including one or more heteroatoms, more preferably Z is an aryl group, most preferably a substituted aryl group in another embodiment Z may be silyl or an alkyl silyl, preferably a trialkyl silyl;

Z may be substituted with R' groups that are independently selected from group consisting of hydrogen or linear, branched, alkyl radicals or cyclic alkyl, alkenyl, alkynyl or aryl radicals. Also, two or more R' groups may be joined to form a cyclic moiety such as an aliphatic or aromatic ring. Preferably R' is an alkyl group having from 1 to 20 carbon atoms, more preferably R' is methyl, ethyl, propyl, butyl, pentyl and the like, including isomers thereof, more preferably R' is a methyl group, or a primary, secondary or tertiary hydrocarbon, including isopropyl, t-butyl and the like, most preferably R' is an isopropyl group. Optionally, an R' group may be joined to A. It is preferred that at least one R' is ortho to X;

A is a bridging group joined to at least one of, preferably both of, X and J.

Bridging group A contains one or more Group 13 to 16 elements from Periodic Table of Elements. More preferably A contains one or more Group 14 elements, most preferably A is a substituted carbon group, a di-substituted carbon group or vinyl group; and In formula (11) m and p are independently an integer from 0 to 5, preferably m is 2; n is the oxidation state of M minus q minus 1 if Q is a monovalent anion, n is (the oxidation state of M–q)/2, if Q is a bivalent anion or n is (the oxidation state of M–q)/3 if Q is a trivalent anion, preferably n is an integer from 1 to 4; and q is 1 or 2, and where q is 2, the two (($R'_m$Z)XA(YJ$R''_m$)) of formula (II) are bridged to each other via a bridging group, preferably a bridging group containing a Group 14 element.

In a preferred embodiment when n is 2 or 3 in formula I or II and the second catalyst is the same as the first catalyst except that one Q group is a hydrocarboxy group, a boronate or an amide. In a particularly preferred embodiment when n is 2 or 3 in formula I or II, then the second catalyst is the same as the first catalyst except that one Q group is an alkoxide, phenoxide, acetylacetonate, carboxylate, cyclopentadienyl, flourenyls or an indenyl group. In another particularly preferred embodiment when n is 2 or 3 in formula I or II the second catalyst is the same as the first catalyst except that one Q group of the second catalyst is a hydrocarboxy adduct of the analogous Q group on the first catalyst, preferably an alkoxide adduct, a boronate, a phenoxide adduct, an acetylacetonate adduct, a carboxylate adduct, an amide adduct, a cyclopentadienyl adduct, a flourenyl adduct or an indenyl adduct.

In preferred embodiment, at least one of the transition metal catalyst compounds is represented by the formula:

$$((Z)XA_t(YJ))_qMQ_mT_s \quad\quad\quad (III)$$

where M is a metal selected from Group 3 to 13 or lanthanide and actinide series of the Periodic Table of Elements; T is bonded to M and is an element from Group 13 to 16, preferably oxygen, boron, nitrogen, silicon, phosphorus, sulfur or aluminum and T may also be bound to one or more C1 to C50 groups optionally containing one or more heteroatoms, preferably T is a hydrocarboxy group, a boronate group or an amide group, preferably an alkoxide, phenoxide, acetylacetonate, or carboxylate or a cyclopentadienide group such as cyclopentadienyls, flourenyls and indenyls, Q is bonded to M and each Q is a monovalent, divalent or trivalent anion; X and Y are bonded to M; X and Y are independently C or a heteroatom, provided that at least one of X and Y is a heteroatom, preferably both X and Y are heteroatoms; Y is contained in a heterocyclic ring J, where J comprises from 2 to 50 non-hydrogen atoms, preferably 2 to 30 carbon atoms; Z is bonded to X, where Z comprises 1 to 50 non-hydrogen atoms, preferably 1 to 50 carbon atoms, preferably Z is a cyclic group containing 3 to 50 atoms, preferably 3 to 30 carbon atoms, alternately Z may be a silyl group, preferably an alkyl silyl group; t is 0 or 1; when t is 1, A is a bridging group joined to at least one of X, Y or J, preferably X and J; q is 1 or 2; m is the oxidation state of M minus q minus s if Q is a monovalent anion, m is (the oxidation state of M–q–s)/2, if Q is a bivalent anion or m is (the oxidation state of M–q–s)/3 if Q is a trivalent anion, preferably m is an integer from 1 to 3, s is 1, 2 or 3, preferably 1 or 2. In one embodiment, where X is oxygen or sulfur then Z is optional. In another embodiment, where X is nitrogen or phosphorous then Z is present. In a preferred embodiment T is oxygen and is bound to an alkyl, aryl, or alkaryl group.

In another embodiment, at least one of the transition metal catalyst compounds is represented by the formula:

 (IV)

where M is a metal selected from Group 3 to 13 of the Periodic Table of Elements, preferably a Group 4 to 12 transition metal, more preferably a Group 4, 5 or 6 transition metal, even more preferably a Group 4 transition metal such as titanium, zirconium or hafnium, and most preferably zirconium;

T is bonded to M and is an element from Group 13 to 16, preferably oxygen, boron, nitrogen, silicon, phosphorus, sulfur or aluminum and T may also be bound to one or more C1 to C50 groups optionally containing one or more heteroatoms, T is preferably a hydrocarboxy group, a boronate, or an amide, preferably an alkoxide, phenoxide, acetylacetonate, or carboxylate or a cyclopentadienide group such as cyclopentadienyls, flourenyls and indenyls.

Each Q is bonded to M and each Q is a monovalent, divalent or trivalent anion.

Preferably each Q is independently selected from the group consisting of halogens, hydrogen, alkyl, aryl, alkenyl, alkylaryl, arylalkyl, hydrocarboxy or phenoxy radicals having 1–20 carbon atoms. Each Q may also be amides, phosphides, sulfides, silylalkyls, diketonates, and carboxylates. Optionally, each Q may contain one or more heteroatoms, more preferably each Q is selected from the group consisting of halides, alkyl radicals and arylalkyl radicals. Most preferably, each Q is selected from the group consisting of arylalkyl radicals such as benzyl.

X and Y are independently C or a heteroatom, provided that at least one of X and Y is a heteroatom, X and Y are preferably each heteroatoms, more preferably independently selected from the group consisting of nitrogen, oxygen, sulfur and phosphorous, even more preferably nitrogen or phosphorous, and most preferably nitrogen;

Y is contained in a heterocyclic ring or ring system J. J contains from 2 to 30 carbon atoms, preferably from 2 to 7 carbon atoms, more preferably from 3 to 6 carbon atoms, and most preferably 5 carbon atoms. Optionally, the heterocyclic ring J containing Y, may contain additional heteroatoms. J may be substituted with R" groups that are independently selected from the group consisting of hydrogen or linear, branched, cyclic, alkyl radicals, or alkenyl, alkynyl, alkoxy, aryl or aryloxy radicals. Also, two or more R" groups may be joined to form a cyclic moiety such as an aliphatic or aromatic ring.

Preferably R" is hydrogen or an aryl group, most preferably R" is hydrogen. When R" is an aryl group and Y is nitrogen, a quinoline group is formed. Optionally, an R" may be joined to A;

Z is a hydrocarbyl group bonded to X, preferably Z is a hydrocarbyl group of from 1 to 50 carbon atoms, preferably Z is a cyclic group having from 3 to 30 carbon atoms, preferably Z is a substituted or unsubstituted cyclic group containing from 3 to 30 carbon atoms, optionally including one or more heteroatoms, Z may be a silyl group, an alkylsilyl group or a trialkyl, in another embodiment Z is not an aryl group;

Z may be substituted with R' groups that are independently selected from group consisting of hydrogen or linear, branched, alkyl radicals or cyclic alkyl, alkenyl, or alkynyl radicals. Also, two or more R' groups may be joined to form a cyclic moiety such as an aliphatic or aromatic ring. Preferably R' is an alkyl group having from 1 to 20 carbon atoms, more preferably R' is methyl, ethyl, propyl, butyl, pentyl and the like, including isomers thereof, more preferably R' is a methyl group or a primary, secondary or tertiary hydrocarbon, including isopropyl, t-butyl and the like, most preferably R' is an isopropyl group. Optionally, an R' group may be joined to A. It is preferred that at least one R' is ortho to X;

A is a bridging group joined to at least one of, preferably both of, X and J.

Bridging group A contains one or more Group 13 to 16 elements from Periodic Table of Elements. More preferably A contains one or more Group 14 elements, most preferably A is a substituted carbon group, a di-substituted carbon group or vinyl group; and In formula (IV) m and p are independently an integer from 0 to 5, preferably m is 2; s is an integer from 1 to 3; and q is 1 or 2, n is the oxidation state of M minus q minus s if Q is a monovalent anion, n is (the oxidation state of M-q-s)/2, if Q is a bivalent anion or n is (the oxidation state of M-q-s)/3 if Q is a trivalent anion, and where q is 2, the two $((R'_mZ)XA(YJR''_m))$ of formula (IV) are bridged to each other via a bridging group, preferably a bridging group containing a Group 14 element.

In one embodiment J is pyridine in any of the above formulae.

In the practice if this invention, two catalysts are selected to produce the desired product. The two or more catalysts are selected from any of the above formulae. For example two different catalyst form formula I may be selected, or a compound from formula I or II and a compound from formula III or IV can be combined, likewise two different catalysts falling with the definition of formula IV may also be combined. In a preferred embodiment a compound from formula I or II is used together with at lease one compound from formulae III or IV. It is possible to obtain a bimodal product by selecting catalysts that are know to produce differing molecular weights.

In a preferred embodiment a first catalyst as represented by formula I or II where at least one Q group is not an oxy-adduct is chosen and the second catalyst is the same as the first catalyst system except that one, two or all three of the Q groups is an oxy-adduct of the same Q group as is present in the first catalyst. For example if [1-(2-Pyridyl)N-1-Methylethyl][1-N-2,6-Diisopropylphenyl Amido] Zirconium Tribenzyl is selected as the first catalyst, them [[1-(2-Pyridyl)N-1-Methylethyl]-[1-N-2,6-Diisopropylphenyl Amido]][2-Methyl-1-Phenyl-2-Propoxy] Zirconium Dibenzyl may be a second catalyst. For purposes of this invention and the claims thereto oxy-adduct is defined to be O—R where O is oxygen and R is a $C_1$ to $C_{50}$ group which optionally may contain one or more heteroatoms. Preferred R groups include t-butyl, t-amyl, t-hexyl, isopropyl, 2-[2-methyl-1-phenyl-propyl], 2-[2-benzyl-butyl], 3-[3-benzyl-pentyl]. Other possible R groups include, benzyl, methyl benzyl, ethyl benzyl and the like. In another embodiment the oxy adduct may be represented by the formula O—B—R, where O is oxygen, B is boron and R is a $C_1$ to $C_{50}$ group which optionally may contain one or more heteroatoms. Preferred R groups include t-butyl, t-amyl, t-hexyl, isopropyl, 2-[2-methyl-1-phenyl-propyl], 2-[2-benzyl-butyl], 3-[3-benzyl-pentyl]. Other possible R groups include, benzyl, methyl benzyl, ethyl benzyl and the like.

In a preferred embodiment the two catalysts, [1-(2-Pyridyl)N-1-Methylethyl][1-N-2,6-Diisopropylphenyl Amido] Zirconium Tribenzyl and [[1-(2-Pyridyl)N-1-Methylethyl]-[1-N-2,6-Diisopropylphenyl Amido]][2-Methyl-1-Phenyl-2-Propoxy] Zirconium Dibenzyl, are used in combination with an alumoxane, preferably a methyl alumoxane, more preferably a modified methyl alumoxane in a gas phase or slurry reactor to produce polyethylene, preferably high density polyethylene or alternately low density polyethylene. In another preferred embodiment a non-coordinating anion, such as tri (n-butyl) ammonium tetrakis (pentafluorophenyl) boron or a trisperfluorophenyl boron, is used in combination with the two catalysts, [1-(2-Pyridyl)N-1-Methylethyl][1-N-2,6-Diisopropylphenyl Amido] Zirconium Tribenzyl and [[1-(2-Pyridyl)N-1-Methylethyl]-[1-N-2,6-Diisopropylphenyl Amido]][2-Methyl-1-Phenyl-2-Propoxy] Zirconium Dibenzyl, in a gas phase or slurry phase reactor to produce polyolefin, preferably polyethylene.

In a preferred embodiment, the two catalyst compounds are typically combined in a ratio of from 0.001:1 to about 10,000:1, preferably 0.5:1 to 1,000:1. In a preferred embodiment the first catalyst is present at from about 0.5 to about 99.5 weight % and the second catalyst is preset at about 99.5 to about 0.5 weight %, based upon the weight of the two catalysts but not activators or supports, preferably 5 to 95 weight % first catalyst and 95 to 5 weight % for the second catalyst, preferably 10 to 90 weight % first catalyst and 90 to 10 weight % for the second catalyst.

In a preferred embodiment the first catalyst is present at from about 0.5 to about 99.5 weight % and the second and third catalysts are preset at about 99.5 to about 0.5 weight %, based upon the weight of the three catalysts but not activators or supports, preferably 5 to 95 weight % first catalyst, preferably 10 to 90 weight % first catalyst.

In a preferred embodiment the component that produces the lower molecular weight is present at 10 ppm to 70 weight % based upon the weight of all the catalysts but not the activators or supports, preferably 100 ppm to 8 weight %, even more preferably 1000 ppm to 5 weight %. In another embodiment the compound that produces the lower molecular weight is present at 30 to 70 weight % based upon the weight of all the catalysts but not the activators or supports, preferably 40 to 60 weight %, even more preferably 45 to 55 weight %.

In another embodiment, the component that makes the low molecular weight portion is present is an amount that will produce 20–70 weight % of the final polymer product.

The two catalysts may be activated at the same or different times, before or after entry into the reactor, and before or after being placed on a support. In one embodiment the two catalysts are activated by the same activator before being placed in the reactor. In another embodiment, one catalyst is activated before being placed in the reactor, and the second catalyst is added, optionally with no activator, the same activator or a different activator. In another embodiment the catalysts are supported on the same support then activated with the same activator prior to being placed in the reactor. In another embodiment the two catalysts are activated with the same or different activators then placed upon a support before being placed in the reactor.

Likewise one or more of the catalyst systems or components may be supported on an organic or inorganic support. Typically the support can be of any of the solid, porous supports. Typical support materials include talc; inorganic oxides such as silica, magnesium chloride, alumina, silica-alumina; polymeric supports such as polyethylene, polypropylene, polystyrene; and the like. Preferred supports include silica, clay, talc magnesium chloride and the like.

Preferably the support is used in finely divided form. Prior to use the support is preferably partially or completely dehydrated. The dehydration may be done physically by calcining or by chemically converting all or part of the active hydroxyls. For more information on how to support catalysts please see U.S. Pat. No. 4,808,561 which teaches how to support a metallocene catalyst system. The techniques used therein are generally applicable for this invention.

The catalysts may be placed on separate supports or may be placed on the same support. Likewise the activator may be placed on the same support as the catalyst or may be placed on a separate support. The catalysts/catalyst systems and/or their components need not be feed into the reactor in the same manner. For example, one catalyst or its components may slurried into the reactor on a support while the other catalyst or components are provided in a solution.

In a preferred embodiment the catalyst system is fed into the reactor in a solution or slurry. Hydrocarbons are useful for the solutions or slurrys. For example the solution can be toluene, hexane, isopentane or a combination thereof such as toluene and isopentane or toluene and pentane. A typical solution would be 0.02 to 0.05 mole catalyst in the hydrocarbon carrier, preferably isopentane or hexane.

In another preferred embodiment the one or all of the catalysts are combined with up to 6 weight % of a metal stearate, (preferably a aluminum stearate, more preferably aluminum distearate) based upon the weight of the catalyst, any support and the stearate, preferably 2 to 3 weight %. In an alternate embodiment a solution of the metal stearate is fed into the reactor. These agents may be dry tumbled with the catalyst or may be fed into the reactor in a solution with or without the catalyst system or its components. In a preferred embodiment the catalysts combined with the activators are tumbled with 1 weight % of aluminum distearate and/or 2 weight % of an antistat, such as a methoxylated amine, such as Witco's Kemamine AS-990 from ICI Specialties in Bloomington, Del. The metal stearate and/or the anti-static agent may be slurried into the reactor in mineral oil, ground into a powder then suspended in mineral oil then fed into the reactor, or blown directly into the reactor as a powder.

More information on using aluminum stearate type additives may be found in U.S. Ser. No. 09/113,216 filed Jul. 10, 1998, which is incorporated by reference herein.

In another embodiment the two catalysts are fed into the reactor separately.

In a preferred embodiment of the invention, (i.e. the combination of (A). [1-(2-Pyridyl)N-1-Methylethyl][1-N-2,6-Diisopropylphenyl Amido] Zirconium Tribenzyl and (B). [[1-(2-Pyridyl)N-1-Methylethyl]-[1-N-2,6-Diisopropylphenyl Amido]][2-Methyl-1-Phenyl-2-Propoxy] Zirconium Dibenzyl with modified methyl alumoxane, it has been noted that temperature appears to affect the balance between the active species. It seems that higher temperatures drive the conversion of one catalyst species to the other. This indicates there are opportunities for controlling the polymer produced by varying the temperature to vary the catalyst species present.

Polymerization Process of the Invention

The catalysts and catalyst systems described above are suitable for use in a solution, gas or slurry polymerization process or a combination thereof, most preferably a gas or slurry phase polymerization process.

In one embodiment, this invention is directed toward the solution, slurry or gas phase polymerization reactions involving the polymerization of one or more of monomers having from 2 to 30 carbon atoms, preferably 2–12 carbon atoms, and more preferably 2 to 8 carbon atoms. Preferred monomers include one or more of ethylene, propylene, butene-1, pentene-1, 4-methyl-pentene-1, hexene-1, octene-1, decene-1, 3-methyl-pentene-1, and cyclic olefins or a combination thereof. Other monomers can include vinyl monomers, diolefins such as dienes, polyenes, norbornene, norbornadiene, vinyl norbornene, ethylidene norbornene monomers. Preferably a homopolymer of ethylene is produced. In another embodiment, a copolymer of ethylene and one or more of the monomers listed above is produced.

In another embodiment ethylene or propylene is polymerized with at least two different comonomers to form a terpolymer. The preferred comonomers are a combination of alpha-olefin monomers having 4 to 10 carbon atoms, more preferably 4 to 8 carbon atoms, optionally with at least one diene monomer. The preferred terpolymers include the combinations such as ethylene/butene-1/hexene-1, ethylene/propylene/butene-1, propylene/ethylene/hexene-1, ethylene/propylene/norbornene and the like.

In a particularly preferred embodiment the process of the invention relates to the polymerization of ethylene and at least one comonomer having from 4 to 8 carbon atoms, preferably 4 to 7 carbon atoms. Particularly, the comonomers are butene-1, 4-methyl-pentene-1,3-methyl-pentene-1, hexene-1 and octene-1, the most preferred being hexene-1, butene-1 and octene-1.

Typically in a gas phase polymerization process a continuous cycle is employed where in one part of the cycle of a reactor system, a cycling gas stream, otherwise known as a recycle stream or fluidizing medium, is heated in the reactor by the heat of polymerization. This heat is removed from the recycle composition in another part of the cycle by a cooling system external to the reactor. Generally, in a gas fluidized bed process for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228 all of which are fully incorporated herein by reference.)

The reactor pressure in a gas phase process may vary from about 10 psig (69 kPa) to about 500 psig (3448 kPa), preferably from about 100 psig (690 kPa) to about 500 psig (3448 kPa), preferably in the range of from about 200 psig (1379 kPa) to about 400 psig (2759 kPa), more preferably in the range of from about 250 psig (1724 kPa) to about 350 psig (2414 kPa).

The reactor temperature in the gas phase process may vary from about 30° C. to about 120° C., preferably from about 60° C. to about 115° C., more preferably in the range of from about 70° C. to 110° C., and most preferably in the range of from about 70° C. to about 95° C. In another embodiment when high density polyethylene is desired then the reactor temperature is typically between 70 and 105° C.

The productivity of the catalyst or catalyst system in a gas phase system is influenced by the main monomer partial pressure. The preferred mole percent of the main monomer, ethylene or propylene, preferably ethylene, is from about 25 to 90 mole percent and the comonomer partial pressure is in the range of from about 20 psia (138 kPa) to about 300 psia (517kPa), preferably about 75 psia (517 kPa) to about 300 psia (2069 kPa), which are typical conditions in a gas phase polymerization process. Also in some systems the presence of comonomer can provide a increase in productivity.

In a preferred embodiment, the reactor utilized in the present invention is capable and the process of the invention is producing greater than 500 lbs of polymer per hour (227 Kg/hr) to about 200,000 lbs/hr (90,900 Kg/hr) or higher of polymer, preferably greater than 1000 lbs/hr (455 Kg/br), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and preferably greater than 65,000 lbs/hr (29,000 Kg/hr) to greater than 100,000 lbs/hr (45,500 Kg/hr), and most preferably over 100,000 lbs/hr (45,500 Kg/hr).

Other gas phase processes contemplated by the process of the invention include those described in U.S. Pat. Nos. 5,627,242, 5,665,818 and 5,677,375, and European publications EP-A-0 794 200, EP-A-0 802 202 and EP-B-634 421 all of which are herein fully incorporated by reference.

A slurry polymerization process generally uses pressures in the range of from about 1 to about 50 atmospheres (15 psi to 735 psi, 103 kPa to 5068 kPa) and even greater and temperatures in the range of 0° C. to about 120° C. In a slurry polymerization, a suspension of solid, particulate polymer is formed in a liquid polymerization diluent medium to which ethylene and comonomers along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process must be operated above the reaction diluent critical temperature and pressure. Preferably, a hexane or an isobutane medium is employed.

In one embodiment, a preferred polymerization technique of the invention is referred to as a particle form polymerization, or a slurry process where the temperature is kept below the temperature at which the polymer goes into solution. Such technique is well known in the art, and described in for instance U.S. Pat. No. 3,248,179 which is fully incorporated herein by reference. The preferred temperature in the particle form process is within the range of about 185° F. (85° C.) to about 230° F. (110° C.). Two preferred polymerization methods for the slurry process are those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In another embodiment, the slurry process is carried out continuously in a loop reactor. The catalyst as a slurry in isobutane or as a dry free flowing powder is injected regularly to the reactor loop, which is itself filled with circulating slurry of growing polymer particles in a diluent of isobutane containing monomer and comonomer. Hydrogen, optionally, may be added as a molecular weight control. The reactor is maintained at a pressure of about 525 psig to 625 psig (3620 kPa to 4309 kPa) and at a temperature in the range of about 140° F. to about 220° F. (about 60° C. to about 104° C.) depending on the desired polymer density. Reaction heat is removed through the loop wall since much of the reactor is in the form of a double-jacketed pipe. The slurry is allowed to exit the reactor at regular intervals or continuously to a heated low pressure flash vessel, rotary dryer and a nitrogen purge column in sequence for removal of the isobutane diluent and all unreacted monomer and comonomers. The resulting hydrocarbon free powder is then compounded for use in various applications.

In another embodiment, the reactor used in the slurry process of the invention is capable of and the process of the invention is producing greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor used in the process of the invention is producing greater than 15,000 lbs of polymer per hour (6804 Kg/hr), preferably greater than 25,000 lbs/hr (11,340 Kg/hr) to about 100,000 lbs/hr (45,500 Kg/hr).

In another embodiment in the slurry process of the invention the total reactor pressure is in the range of from 400 psig (2758 kPa) to 800 psig (5516 kPa), preferably 450 psig (3103 kPa) to about 700 psig (4827 kPa), more preferably 500 psig (3448 kPa) to about 650 psig (4482 kPa), most preferably from about 525 psig (3620 kPa) to 625 psig (4309 kPa).

In yet another embodiment in the slurry process of the invention the concentration of ethylene in the reactor liquid medium is in the range of from about 1 to 10 weight percent, preferably from about 2 to about 7 weight percent, more preferably from about 2.5 to about 6 weight percent, most preferably from about 3 to about 6 weight percent. Another process of the invention is where the process, preferably a slurry or gas phase process is operated in the absence of or essentially free of any scavengers, such as triethylaluminum, trimethylaluminum, tri-isobutylaluminum and tri-n-hexylaluminum and diethyl aluminum chloride, dibutyl zinc and the like. This process is described in PCT publication WO 96/08520 and U.S. Pat. No. 5,712,352, which are herein fully incorporated by reference.

In another embodiment the process is run with scavengers. Typical scavengers include trimethyl aluminum, tri-isobutyl aluminum and an excess of alumoxane or modified alumoxane.

The proportions of the components of the feed catalyst solution can be varied to alter molecular weight and other properties. For example altering the catalyst ratios will alter flow index, melt index, melt flow ratio and/or density. For example, in a system where a catalyst represented by formula I and a catalyst represented by formula IV are combined, if the proportion of a catalyst represented by formula IV is increased then, more lower molecular weight material is produced thus increasing flow index, altering the molecular weight distribution. In a preferred embodiment the catalyst that produces the lower molecular weight component is present at a value to produce 45–65 weight % of the final polymer product. For pipe and film applications the combination of 55–35 weight % of (A). [1-(2-Pyridyl)N-1-Methylethyl][1-N-2,6-Diisopropylphenyl Amido] Zirconium Tribenzyl and 45–65 weight % of (B). [[1-(2-Pyridyl)N-1-Methylethyl]-[1-N-2,6-Diisopropylphenyl Amido]][2-Methyl-1-Phenyl-2-Propoxy] Zirconium Dibenzyl has been found effective.

Another method to alter the molecular weight is to add hydrogen to the system by increasing the hydrogen ethylene ratio. A method to control the density is altering the comonomer content.

A method to control molecular weight distribution (Mw/Mn), flow index, and/or density comprising altering on line in a commercial scale gas phase reactor (i.e. having a volume of 1500 cubic feet or more) the reaction temp and/or the catalyst ratio in the intimately mixed catalyst solution and/or the hydrogen concentration and/or the activator to transition metal ratio, such as the aluminum/zirconium ratio is also provided herein.

Injection and mixing temperatures also provide a means to alter product properties as temperature affects activation and/or solvent evaporation and thus alters the catalyst composition and hence alters the final product.

The sequence and timing of activation also provides an opportunity to alter the catalyst composition and thus the final product. For example higher concentrations of methyl alumoxane in a system comprising (A). [1-(2-Pyridyl)N-1-Methylethyl][1-N-2,6-Diisopropylphenyl Amido] Zirconium Tribenzyl and (B). [[1-(2-Pyridyl)N-1-Methylethyl]-[1-N-2,6-Diisopropylphenyl Amido]][2-Methyl-1-Phenyl-2-Propoxy] Zirconium Dibenzyl will alter the balance of products formed by the two catalysts. This includes higher concentrations during activation and/or mixing and/or transport and/or in spraying into the reactor. Likewise we have noted that increasing the hydrocarbon carrier in the catalyst feed increased the amount of lower molecular weight fraction produced.

One can also vary the product by altering the reaction temperature. We have noted that raising the reaction temperature increased the amount of the higher molecular weight component and unusually the two modes in the size exclusion chromatography graph moved closer together (that is the Mw/Mn became lower when compared to the same system at a lower temperature).

One can also vary the molecular weight distribution by varying the reactor temperature, varying the temperature of the catalyst system before it enters the reactor, varying the catalyst to activator ratio, varying the volume of the carrier, and/or contacting the transition metal component with solvent prior to activation with the activator.

In a preferred embodiment the ratio of the first catalyst to the second catalyst is 5:95 to 95:5, preferably 25:75 to 75:25, even more preferably 40:60 to 60:40.

In another preferred embodiment the catalyst system in is liquid form and is introduced into the reactor into a resin particle lean zone. For information on how to introduce a liquid catalyst system into a fluidized bed polymerization into a particle lean zone, please see U.S. Pat. No. 5,693,727, which is incorporated by reference herein.

An example of a typical polymerization is: modified methylalumoxane in hydrocarbon such as hexane or isopentane (about 1 to 10% aluminum) and 10–30 weight % of [1-(2-Pyridyl)N-1-Methylethyl][1-N-2,6-Diisopropylphenyl Amido] Zirconium Tribenzyl and 70–90 weight % grams of [[1-(2-Pyridyl)N-1-Methylethyl]-[1-N-2,6-Diisopropylphenyl Amido]][2-Methyl-1-Phenyl-2-Propoxy] Zirconium Dibenzyl, are suspended in solution then dried, thereafter they are tumbled with 2 weight % aluminum distearate and then slurried into a fluidized bed gas phase reactor held at a temperature of about 85 to about 100° C.—in an Al to Zr ratio of about 500:1 to about 1000:1, thereafter ethylene gas is sparged into the reactor to maintain a partial pressure of 70 to 100 psi, the reactor is then allowed to run for about 30 minutes. Polyethylene having a melt index of between 0.01 to 10 dg/min is recovered.

In a preferred embodiment, the polyolefin recovered typically has a melt index as measured by ASTM D-1238, Condition E, at 190° C. of 1 g/10 min or less. In a preferred embodiment the polyolefin is ethylene homopolymer or copolymer. The comonomer is preferably a C3 to C20 linear branched or cyclic monomer, and in one embodiment is a C3 to C12 linear or branched alpha-olefin, preferably propylene, hexene, pentene, hexene, heptene, octene, nonene, decene, dodecene, 4-methyl-pentene-1, 3-methyl pentene-1, 3,5,5-trimethyl hexene 1, and the like.

In a preferred embodiment the catalyst system described above is used to make a high density polyethylene having a density of between 0.925 and 0.965 g/cm$^3$ (as measured by ASTM 2839), and/or a melt index of 1.0 or less g/10 min or less (as measured by ASTM D-1238, Condition E, at 190° C.). In another embodiment the catalyst system described above is used to make a polyethylene of 0.85 to 0.924 g/cm$^3$.

In another embodiment the polymer produced by this invention has a molecular weight distribution (Mw/Mn) of at least 10, preferably at least 15, preferably at least 20, even more preferably at least 30.

Further, while not wishing to be bound by any theory, it is believed that the polymers produced by this invention have the unique advantage of the two polymer products being so intimately blended that there is an even distribution of the two polymers across the polymer particles as they exit the reactor. The unprocessed, untreated granular polymer is referred to as neat polymer.

The neat polymer is then separated into fractions by standard sieves sizes according to ASTM D 1921 particle size (sieve analysis) of plastic materials Method A or PEG method 507.

| Sieve size | Fraction Collected | Fraction Name |
| --- | --- | --- |
| 10 mesh | >2000 μm | Fraction 1 |
| 18 mesh | 2000–1000 μm | Fraction 2 |
| 35 mesh | <1000–500 μm | Fraction 3 |
| 60 mesh | <500–250 μm | Fraction 4 |
| 120 mesh | <250–125 μm | Fraction 5 |
| pan | <125 μm | Fraction 6 |

The individual fractions (Fraction 1, 4, 6) are then tested for physical properties. Melt index is measured according to ASTM 1238, condition e, 190° C. Crystallinity is measured using X-ray diffraction as described in example 13 below.

A unique attribute of the polymer produced herein is that the melt indices of the different fractions do not vary significantly. In a preferred embodiment the melt indices of Fractions 1, 4 and 6 do not vary by more than 20% relative, preferably by not more than 15% relative, preferably by not more than 10% relative, preferably by not more than 8% relative, preferably by not more that 6% relative, preferably by not more than 4% relative. Relative means relative to the mean of the values for Fractions 1, 4 and 6.

Another unique attribute of the polymer produced herein is that the percent crystallinity of the different fractions do not vary significantly. In a preferred embodiment the percent crystallinity of Fractions 1, 4 and 6 do not vary by more than 6% relative, preferably by not more than 5% relative, preferably by not more than 4% relative, preferably by not more than 3% relative, preferably by not more that 2% relative. Relative means relative to the mean of the values for Fractions 1, 4 and 6.

Another unique attribute of the polymer produced herein is that the Mw/Mn of the different fractions do not vary significantly. In a preferred embodiment the Mw/Mn of Fractions 1, 4, 5 and 6 do not vary by more than 20% relative, preferably by not more than 10% relative, preferably by not more than 8% relative, preferably by not more than 6% relative, preferably by not more that 4% relative, preferably by not more than 2% relative. Relative means relative to the mean of the values for Fractions 1, 4 and 6. Mn and Mw were measured by gel permeation chromatography on a waters 150° C. GPC instrument equipped with differential refraction index detectors. The GPC columns were calibrated by running a series of narrow polystyrene standards and the molecular weights were calculated using broad polyethylene standards National Bureau of Standards 1496 for the polymer in question.

In another embodiment the polymer produced herein has an Mw/Mn of 8 or more, preferably 10 or more, preferably 12 or more.

In another embodiment a parameter of polymer produced is that the crystallite morphology varies with particle size. Fraction 1 preferably has an aspect ratio of 0.5–1.5, fraction 4 has an aspect ratio of 1.2 to 4, Fraction 6 has an aspect ratio of about 1.75 to 5 provided that the fractions differ by at least 0.3, preferably by at least 0.5, more preferably by about 1.0. In one embodiment the aspect ratio of Fraction 1< aspect ration of Fraction 4< the aspect ratio of Fraction 6. The aspect ratio is [<110>/<011>] as discussed below in example 13.

In another preferred embodiment the polymer produced according to this invention comprises 10–90 weight % of low molecular weight polymer (low is 50,000 or less preferably 40,000 or less), preferably 20 to 80 weight %, more preferably 40–60 weight %, based upon the weight of the polymer.

In another embodiment of this invention the polymer produced is bi- or multi-modal (on the SEC graph). By bi- or multi-modal is meant that the SEC graph of the polymer has two or more positive slopes, two or more negative slopes, and three or more inflection points (an inflection point is that point where the second derivative of the curve becomes negative) OR the graph has at least has one positive slope, one negative slope, one inflection point and a change in the positive and or negative slope greater than 20% of the slope before the change. In another embodiment the SEC graph has one positive slope, one negative slope, one inflection point and an Mw/Mn of 10 or more, preferably 15 or more, more preferably 20 or more. The SEC graph is generated by gel permeation chromatography on a waters 150° C. GPC instrument equipped with differential refraction index detectors. The columns were calibrated by running a series of narrow polystyrene standards and the molecular weights were calculated using Mark Houwink coefficients for the polymer in question.

The polyolefins then can be made into films, molded articles, sheets and the like. The films may be formed by any of the conventional technique known in the art including extrusion, co-extrusion, lamination, blowing and casting. The film may be obtained by the flat film or tubular process which may be followed by orientation in an uniaxial direction or in two mutually perpendicular directions in the plane of the film. Particularly preferred methods to form the polymers into films include extrusion or coextrusion on a blown or cast film line.

The films produced may further contain additives such as slip, antiblock, antioxidants, pigments, fillers, antifog, UV stabilizers, antistats, polymer processing aids, neutralizers, lubricants, surfactants, pigments, dyes and nucleating agents. Preferred additives include silicon dioxide, synthetic silica, titanium dioxide, polydimethylsiloxane, calcium carbonate, metal stearates, calcium stearate, zinc stearate, talc, BaSO$_4$, diatomaceous earth, wax, carbon black, flame retarding additives, low molecular weight resins, glass beads and the like. The additives may be present in the typically effective amounts well known in the art, such as 0.001 weight % to 10 weight %.

The films produced using the polymers of this invention have extremely good appearance properties. The have a low gel content and/or have good haze and gloss. In a preferred embodiment the 1 mil film (1.0 mil=0.25 mm) has a 45° gloss of 7 or more, preferably 8 or more as measured by ASTM D 2475. In a preferred embodiment the 1 mil film (1.0 mil=0.25 mm) has a haze of 75 of less, preferably 70 or less as measured by ASTM D 1003, condition A.

EXAMPLES

MFR Melt Flow Ratio was measured by ASTM 1238.
BBF (butyl branch frequency per 1000 carbon atoms) was measured by infrared spectroscopy as describe in U.S. Pat. No. 5,527,752.
PDI (polydispersity index) is equivalent to Mw/Mn and was measured by Size Exclusion Chromolograph
Mn and Mw were measured by gel permeation chromatography on a waters 150° C. GPC instrument equipped with differential refraction index detectors. The GPC columns were calibrated by running a series of narrow polystyrene standards and the molecular weights were calculated using Mark Houwink coefficients for the polymer in question.
Melt Index (MI) was measured by the procedure according to ASTM 1238, condition E.
Melt Index Ratio (MIR) is the ratio of $I_{21}$ over $I_2$ as measured by the procedure according to ASTM D 1238.
Density is measured according to ASTM D 1505.

Example 1

Preparation of [1-(2-Pyridyl)N-1-Methylethyl][1-N-2,6-Diisopropylphenyl]Amine

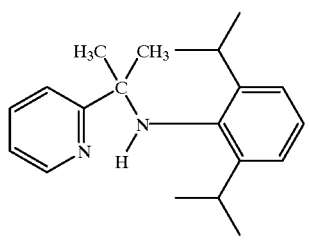

In a dry box, 22.45 mmol (6.34 g) 2-acetylpyridine(2,6-diisopropylphenylimine) were charged to a 250 mL round bottom flask equipped with a stir bar and septa. The flask was sealed, removed from the dry box and placed under nitrogen purge. Dry toluene (50 mL) was added and stirred to dissolve the ligand. The vessel was chilled to 0° C. in a wet ice bath. Trimethyl aluminum (Aldrich, 2.0 M in toluene) was added dropwise over ten minutes. The temperature of the reaction was not allowed to exceed 10° C. When addition of the trimethyl aluminum was complete, the mixture was allowed to warm slowly to room temperature, and then was then placed in an oil bath and heated to 40° C. for 25 minutes. The vessel was removed from the oil bath and placed in an ice bath. A dropping funnel containing 100 mL of 5% KOH was attached to the flask. The caustic was charged to the reaction dropwise over a 1 hour span. The mixture was transferred to a separatory funnel. The aqueous layer was removed. The solvent layer was washed with 100 mL water then 100 mL brine. The red-brown liquid product was dried over $Na_2SO_4$, vacuum stripped and placed under high vacuum over night.

80 mL of red-brown liquid was transferred to a 200 mL Schlenk flask equipped with a stir bar. A distillation head with a dry ice condenser was attached to the flask. The mixture was vacuum distilled yielding approximately 70 g of dark yellow viscous liquid product.

Example 2

Preparation of [1-(2-Pyridyl)N-1-Methylethyl][1-N-2,6-Diisopropylphenyl Amido]Zirconium Tribenzyl

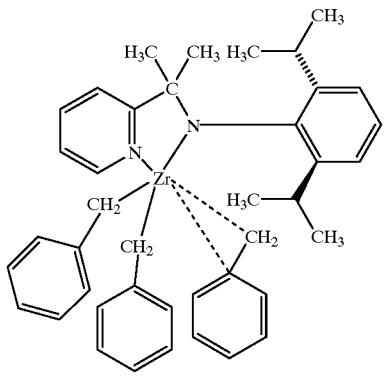

In a darkened room and darkened dry box, 5.0 mmol (1.45 g) of the ligand made in Example 1 were charged to a 100 mL Schlenk tube equipped with a stir bar. The ligand was dissolved in 5 mL of toluene. To a second vessel equipped with a stir bar was charged 5.5 mmol (2.5 g) tetrabenzyl zirconium and 10 mL toluene.

The ligand solution was transferred into the tetrabenzyl zirconium solution. The vessel was covered with foil and allowed to stir at room temperature in the dry box. After 6 hours at room temperature 80 mL dry hexane was added to the reaction solution and allowed to stir overnight. The reaction mixture was filtered through a medium porosity frit with approximately 2 g pale yellow solids collected.

Example 3

Preparation of [[1-(2-Pyridyl)N-1-Methylethyl][1-N-2,6-Diisopropylphenyl Amido]][2-Methyl-1-Phenyl-2-Propoxy]Zirconium Dibenzyl

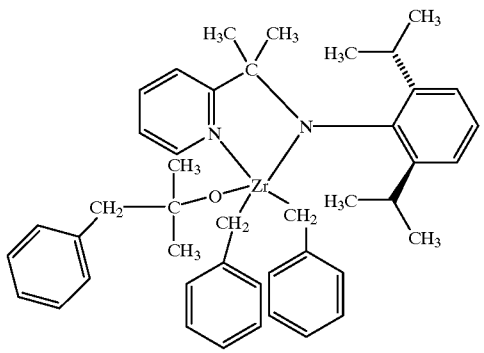

To an oven-dried, cooled, purged and sealed GC vial was charged 0.10 mL dried acetone. The GC vial was sealed in a shell vial and taken into the dry box. In a darkened room and darkened dry box 2.0 mmol (1.3 g) of the material made in Example 2 and 9 mL toluene were charged to 1 100 mL Schlenk flask equipped with a stir bar. To a second GC vial was charged 2.0 mmol (146 uL) acetone and 1.0 mL toluene. The acetone/toluene solution was transferred dropwise via syringe into the stirred solution of [1-(2pyridyl) N-1-methylethyl][1-N-2,6-diisopropylphenylamido]zirconoum tribenzyl. The vessel was covered with foil and allowed to stir at room temperature in the dry box overnight.

The reaction solution was vacuum stripped to a tacky orange residue. Dry hexane (20 mL) was added and the residue stirred vigorously, then vacuum stripped again to a yellow-orange glass. Hexane was added again and vigorously stirred. The vessel was placed in a freezer (−24° C.) for approximately 2 hours. The mixture was filtered through a medium porosity frit. Pale yellow solids (0.8 g) were collected. Slow deliberate feeding of the acetone with good mixing appears best.

Example 4

A series of bimodal ethylene/hexene copolymers were made in a laboratory scale, slurry phase reactor using mixed catalyst compositions of the complexes prepared in Example 2 and Example 3 according to the invention with modified methyl alumoxane (MMAO) cocatalyst type 3A (commercially available from Akzo Chemicals, Inc. under the trade name Modified Methylalumoxane type 3A, covered under U.S. Pat. No. 5,041,584).

In each case, the catalyst composition was prepared by preparing mixtures of the complexes from Example 2 and Example 3 in toluene, and then contacting with MMAO solution (7.0 wt % Al in heptane) in the presence of 0.1 mL 1-hexene. Polymerization reaction conditions were 85° C., 85 psi (586 kPa) ethylene, 43 mL of 1-hexene, 0.5 micromole Zr, and a MMAO/Zr mole ratio of 1,000:1. Complex ratios are expressed as the mole ratios of the complex prepared in Example 3 to the complex prepared in Example 2. Results are shown in Table 1 below.

TABLE 1

| Complex Ratio | Activity gPE/mmolcat/ 100 psi C2/hr | I2 dg/min | MFR | BBF per 1000 C3 s | PDI |
|---|---|---|---|---|---|
| 100:0 | 139765 | 162.2 | 1.82 | 6.28 | 11.18 |
| 90:10 | 291765 | 13.49 | 61.66 | 10.08 | 25.84 |
| 80:20 | 175529 | 0.05 | 1,027 | 7.54 | 23.74 |
| 60:40 | 235765 | 0.0085 | 317.4 | 9.92 | 28.24 |
| 50:50 | 189647 | 0.012 | 173.1 | 11.01 | 30.25 |

Size Exclusion Chromatography was conducted on the resins prepared in Table 1. The results clearly demonstrate an increase in the high molecular weight component with increasing concentrations of the complex from Example 2. The relative amounts of the complexes from Example 3 and Example 2 respectively reflect the low and high molecular weight components in these bimodal resins. This shows that the two catalysts are highly compatible.

Example 5

An ethylene hexene copolymer was produced in a 14 inch pilot plant gas phase reactor operating at 85° C., 220 psi (1517 kPa) having a water cooled heat exchanger. The ethylene was fed in at a rate of about 55 pounds of ethylene per hour (25 kg/hr) and hexene was fed in at 1.4 pounds per hour(0.64 kg/hr) and hydrogen was fed in at rate of 0.021 pounds per hour (0.01 kg/hr) to make about 35 pounds per hour (15.9 kg/hr) of polymer. Total reactor pressure was 350 psi (2413 kPa). The nitrogen was present at about 3–7 pounds/hour (1.4 kg–3.2 kg). The reactor was equipped with a plenum set at 1800 pounds per hour (818.2 kg/hr) with a single hole tapered nozzle injector having a 0.55 inch (1.4 cm) ID diameter. (The plenum is a device used to create a particle lean zone in a fluidized bed gas phase reactor. For more information on plenum usage see U.S. Pat. No. 5,693,727). This procedure was repeated and one or more of the reaction temperature, the Al/Zr ratio, the reaction temperature, the injection temperature or the hydrocarbon feed carrier were varied as reported in Table 2.

TABLE 2

| Example | Rxn temp | Wt % low MW | Catalyst | Mw/Mn | Al:Zr ratio |
|---|---|---|---|---|---|
| A | 85 | 60 | 3 | 14 | 350:1::Al:Zr |
| B | 90 | 57 | 3 | 16 | 360:1::AL:Zr |
| C | 95 | 51 | 3 | 12 | 350:1::Al:Zr |
| D | 105 | 35 | 3 | 11 | 350:1::Al:Zr |
| E | 85 | 22 | 60/40 2:3 | | 450:1::Al:Zr |
| F | 85 | 70 | 3 | | 72:1::Al:Zr |

"Wt % low Mw" is the weight % of the lower molecular weight species produced as characterized by Size Exclusion Chromatography using a log normal Gaussian deconvolution.

Example 6

The example above was repeated with the catalysts produced in examples 2 and 3 except that the polymerization conditions were 85° C., 220 psi (1517 kPa)$C_2$, 500:1 Al/Zr, catalyst feed 10 cc/hr, MMAO feed 300 cc/hr (2.3 wt % Al in hexane). The ratio of the two catalysts was varied.

TABLE 3

| Catalyst ratio 2/3 | Activity (g PE/mmolZr/hr) | I2 dg/min | MFR | density g/cm$^3$ |
|---|---|---|---|---|
| 60/40 | 15,651 | 0.196 | 51.47 | 0.9455 |
| 40/60 | 17,929 | 0.150 | 59.89 | 0.9475 |
| 20/80 | 16,905 | 0.165 | 63.45 | 0.9498 |
| 0/100 | 16,061 | 0.167 | 76.27 | 0.951 |
| 80/20 | 40,048 | 0.150 | 52.08 | 0.9422 |

Example 7

Two ethylene hexene copolymers were produced in an 8 foot (2.4 m) diameter gas phase reactor (having a volume of about 2000 cubic feet) having a bed height of 38 feet(11.6 m). The ethylene feed rate was about 8000 to 9000 pounds per hour (3636–4090 kg/hr). The hexene feed rate was about 200–230 pounds per hour (90.0–104.5 kg/hr). The hydrogen feed rate was about 1–2 pounds per hour (2.2 to 4.4 kg/hr). The copolymer was produced at 8000–9000 pounds per hour(3636–4090 kg/hr). 30–60 pounds per hour of nitrogen (13.6–27.3 kg/hr) were fed into the reactor. The reactor was equipped with a plenum set at 50,000 pounds per hour (22,727 kg/hr) and three hole nozzle having a diameter of 0.125 inches (0.32 cm) tapering to a diameter of 0.05 inches (0.13 cm) at the central hole and two other holes 0.30 inches (0.76 cm)from the nozzle end perpendicular to the flow of the gas and 5/64 ths of an inch (0.20 cm)wide. The cycle gas velocity was about 2–2.2 feet per sec (60–67 cm/sec). The injection temperature was 22° C. for the first run and 80° C. for the second run. The catalyst was the catalyst produced in example 3 combined with 2 weight % modified methyl alumoxane 3A in an Al:Zr ratio of 150:1. The first run produced an ethylene hexene copolymer having 44 weight % lower molecular weight portion and the second run produced 36 weight % of lower molecular weight portion.

Example 8

Five 0.02 Molar solutions in toluene of the compounds prepared in examples 2 and 3 were prepared in ratios of 80/20, 60/40, 40/60, 20/80 and 0/100. They were polymerized according to the procedure in example 5 using modified methyl alumoxane 3A as the cocatalyst. The bed temperature was maintained at 85° C. The ethylene partial pressure was 220 psi (1537 kPa) and the Al:Zr ratio was 500:1.

|  | 80/20 | 60/40 | 40/60 | 20/80 | 0/100 |
| --- | --- | --- | --- | --- | --- |
| C6/C2 Ratio ($\times 10^{-3}$) | 8.1–9.1 | 6.6–7.7 | 6.1–6.7 | 5.4–5.6 | 5.4–5.7 |
| H2/C2 Ratio ($\times 10^{-3}$) | 23.7–25.5 | 17.5–18.6 | 14.0 | 12.3–12.6 | 12.1–12.2 |
| Production Rate (pph) | 28 | 26 | 26 | 26 | 27 |
| Activity GPE/mmolZr/h | 19000 | 17500 | 15000 | 16100 | 17500 |
| Melt Index dg/min | 0.15–0.26 | 0.17–0.26 | 0.13–0.34 | 0.12–0.17 | 0.16–0.21 |
| Flow Index dg/miN | 8.07–12.3 | 0.95–12.88 | 8.81–14.07 | 9.68–10.95 | 12.53–14.50 |
| Melt Flow Ratio MFR | 39.87–55.63 | 46.37–64.39 | 32.96–65.75 | 61.24–81.87 | 70.73–77.83 |
| Density g/cc | 0.942–0.944 | .0945–0.947 | 0.947–0.950 | 0.950–0.951 | 0.9951–0.952 |

Example 9

Synthesis of [1-(2-Pyridyl)-N-1-Methylethyl][1-N-2,6Diisopropylphenylamido][3-Benzyl-3-Pentoxy] Zirconium Dibenzyl Diethyl ketone (40 mmol, 4.0 mL, Aldrich, 3-Pentanone, 99.5%, [86.13]) was dissolved in 96 mL of dry toluene. The diethyl ketone solution was slowly transferred into a stirring solution (400 mL, 0.125M in toluene) of the complex prepared in Example 2. The resulting solution was allowed to stir over night.

Example 10

Synthesis of [1-(2-Pyridyl)-N-1-Methylethyl][1-N-2,6Diisopropylphenylamido][2-Benzyl-2-Butoxy] Zirconium Dibenzyl Methyl ethyl ketone (40 mmol, 3.6 mL, Aldrich, 2-Butanone, 99.5%, [72.11]) was dissolved in 100 mL of dry toluene. The methyl ethyl ketone solution was slowly transferred into a stirring solution (400 mL, 0.125M in toluene), of the complex prepared in Example 2. The resulting solution was allowed to stir over night.

Example 11

Figure 6:
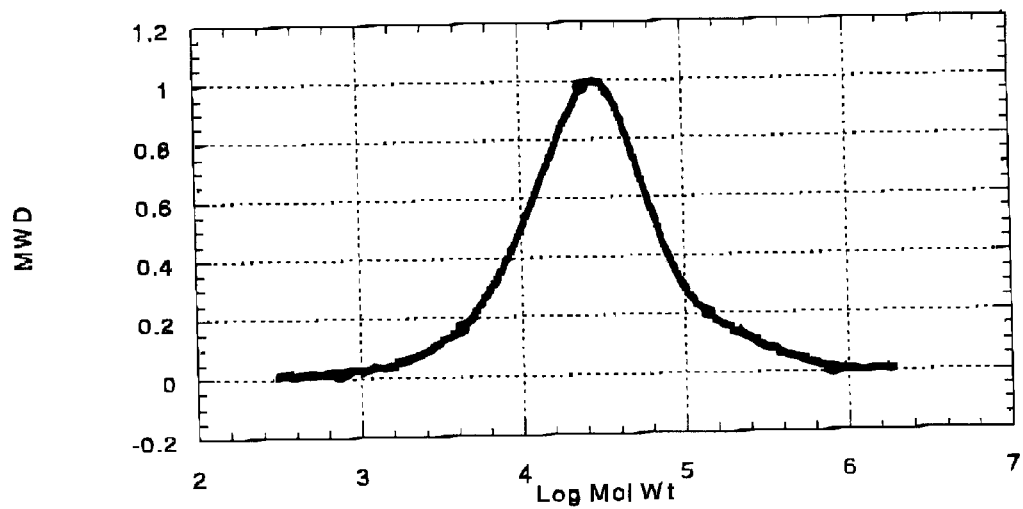
FIGS. 6 and 7 are the size exclusion chromatography (SEC) graphs for the runs in examples 11 and 12.

In a dry box, 1-hexene (0.1 mLs, alumina dried) was charged to an oven dried, 4 dram glass vial. The complex from Example 2 (0.25 micromoles, 2.0 microliters, a 0.125M solution in toluene), and the complex prepared in Example 9 (0.25 µmoles, 3.7 microliters, a 0.067M solution in dueterated benzene) was added to the 1-hexene resulting in a pale yellow solution. MMAO type 3A (0.25 mmoles) was then added to the vial resulting in a pale yellow reaction solution. The reaction solution was charged to the reactor containing 600 mLs n-hexane, 43 mLs 1-hexene, and 0.13 mLs (0.25 mmoles) MMAO type 3A, and run at 70° C., 85 psi ethylene, and 10 psi hydrogen for 30 minutes. The reaction produced 26.3 g of polyethylene resin (activity= 123765 g polyethylene/mmole Zr/hour/100 psi ethylene, I2=28.49, I21=838, MFR=29.4, BBF=7.63). Size Exclusion Chromatography (SEC) revealed the following molecular weight Results: Mn=12611, Mw=50585, PDI=4.01. The SEC graph is presented as FIG. 6.

Example 12

Figure 7:
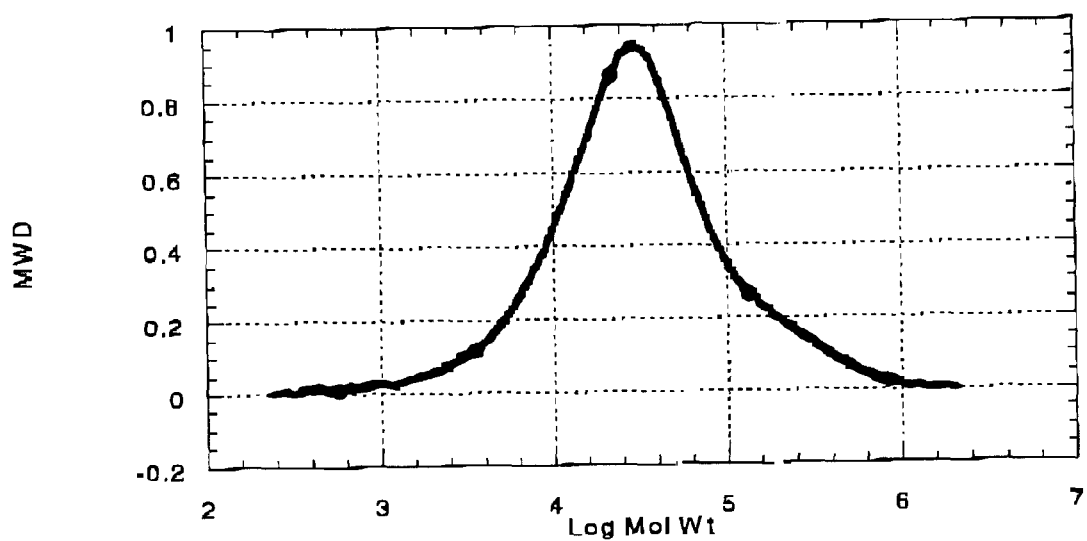

In a dry box, 1-hexene (0.1 mLs, alumina dried) was charged to an oven dried, 4 dram glass vial. The complex from Example 2 (0.25 µmoles, a 0.125M solution in toluene), and the complex from Example 10 (0.25 µmoles, an 0.080M solution in toluene) was added to the 1-hexene resulting in a yellow solution. MMAO type 3A (0.25 mmoles) was then added to the vial resulting in yellow reaction solution. The reaction solution was charged to a 1L slurry reactor containing 600 mLs n-hexane, 43 mLs 1-hexene, and 0.13 mLs (0.25 mmoles) MMAO type 3A, and run at 70° C., 85 psi ethylene, and 10 psi hydrogen for 30 minutes. The reaction produced 30.7 g of resin (activity= 144471 g polyethylene/mmole Zr/hour/100 psi ethylene, I2=11.47, I21=468, MFR=40.8, BBF 7.53).: Size Exclusion Chromatography (SEC) revealed the following molecular weight Results: Mn=12794, Mw=62404, PDI=4.88. The SEC graph is presented as FIG. 7.

Example 13

An ethylene hexene copolymer (A) having a density of about 0.946 g/cc was produced according to the procedure in example 5 except that the catalyst from example 3 was added at a rate of 9 cc/hour and the catalyst from example 2 was fed at fed at rate of 1 cc/hour (90:10 ratio). Hexene was fed at about 0.8–0.9 lbs (0.36–0.41 kg) per hour, ethylene was fed at a rate of about 41 to 43 pounds (18.5–19.4 kg) per hour. Hydrogen was fed at a rate of about 17–20 millipounds (7.7–9.1 g) per hour and the hexane carrier was fed at a rate of about 100 cc/hour. The ethylene partial pressure was 120 psi (827 kPa) and the reactor temperature was 75° C. The aluminum zirconium ratio was Al:Zr::300:1.

Another ethylene hexene copolymer (B) was produced using the same procedure except that only the catalyst from example 3 was fed into the reactor (10 cc/hr), the reactor temperature was 95° C., hydrogen was fed at a rate of 12–14 millipounds (5.4–6.4 g)per hour, the ethylene feed was fed at 41 to 45 pounds (18.5–20.3 kg)per hour and the ethylene partial pressure was 220 psi(827 kPa). The copolymer had a density of 0.951 g/cc Another ethylene hexene copolymer (C) was produced using the same procedure except that only the catalyst from example 3 was fed into the reactor (12 cc/hr), the reactor temperature was 95° C., hydrogen was fed at a rate of 12–13 millipounds (5.4–5.9 g)per hour, the ethylene feed was fed at 44 to 47 pounds (19.9–21.2 kg)per hour, the ethylene partial pressure was 220 psi(827 kPa), and the hexane carrier was fed in at a rate of 70/cchr. The copolymer had a density of 0.951 g/cc.

These copolymers were then fractionated using the following sieves:

| Sieve size | Fraction Collected | Fraction Name |
|---|---|---|
| 10 mesh | >2000 μm | Fraction 1 |
| 18 mesh | 2000–1000 μm | Fraction 2 |
| 35 mesh | <1000–500 μm | Fraction 3 |
| 60 mesh | <500–250 μm | Fraction 4 |
| 120 mesh | <250–125 μm | Fraction 5 |
| pan | <125 μm | Fraction 6 |

The fraction were then characterized as reported in tables A, B, C and D.

Summary of the Experimental Procedure used for X-ray Diffraction Data Collection and Techniques used for Percent Crystallinity and Crystallite Morphology Analysis X-ray Diffraction Data Collection A Siemens GADDS X-ray diffraction (XRD) unit equipped with a Copper X-ray tube source ($\lambda$=1.54056 Å) running at a power setting of 40 kV and 40 mA, a graphite monochromater, a 0.3 mm collimator prior to the sample and a multi-wire General Area Diffraction Detector (GADD) with a sample-detector distance of 15 cm was the condition used for all data collection. Large individual particles were glued to a thin glass rod which allowed the particle to be suspended and rotated in the beam without any contribution form the glass rod or glue. Fine particles were placed in a thin silica, capillary for the analysis. All data collection was done in transmission mode with a beam stop 3 cm behind the sample. Spectra were collected at three different diffractometer setting with the detector covering the following 2θ regions, 4°–34°, 32°–58° and 56°–76°, with collection times typically of 600 s per region. These three different regions were unwarped (distortion correction) and then spliced together to form a single spectra covering 4°–76° 2θ. The GADDS system at the 15 cm sample-detector distance provided a view of ~120° arc of the Debye ring. This clearly showed a uniform intensity along the ring which is indicative of a perfectly random homogeneous structure showing no presence of preferred orientation or texturing.

Curve Fitting

The full profile curve fitting program supplied with the GADDS system was used for peak profile fitting to the spectra. For large particles an air scatter pattern collected under the same conditions was subtracted from the experimental data prior to fitting, in the case of small particles a spectra combining the blank silica capillary and air scatter was subtracted from the experimental data prior to fitting. Four components were used to fit the diffraction data; (i) diffraction peaks were fitted with a pseudo-voigt profile-shape-function with a mixing parameter of 1, (ii) amorphous peaks were fitted with a Lorentzian profile-shape-function with the FWHM (full width half maximum) of the peak and peak positions being fixed based upon amorphous scattering simulations, (iii) a paracrystalline component was fitted with a Pearson VII profile-shape-function with an exponent of 50 and (iv) a linear fit for the compton scattering.

Once the Compton scattering was subtracted from the data, the total diffracted intensity in the pattern was fit with three components, (1) amorphous intensity $I_{am}$, (2) paracrystalline component $I_{para}$ and (3) crystalline diffraction peaks $I_{xal}$. The following expression was then used to calculate the percent crystallinity:

Percent Crystallinity=$I_{xal}/(I_{am}+I_{para}+I_{xal})\times 100$

Crystallite Size

The crystallite size was measured using the peak-width at half maximum intensity of the {110} and {011} reflections in X-ray diffraction patterns from granular polyethylene resin. These two values allow the size of the crystallite in the given crystallographic direction to be calculated using the Scherrer equation:

Crystallite Size $(t)=0.9\lambda/B' \cos \theta_B$ $B'=B_{measured}-B_{instrumental\ broadening}$ Where $\lambda$ is the wavelength of the incident X-ray, B' is the corrected peak width in radians at half maximum intensity (the instrumental beam broadening component was measured using a National Bureau of Standards SRM 660 Lanthanum Hexaboride sample)), $\theta_B$ is the peak position and t is the size of the crystal in the crystallographic direction based upon the reflection of interest. The <110> reflection provides crystallite size information in the <110> direction that lies in the ab plane of the PE orthorhombic crystal, similarly the {011} reflection provides crystallite size data in the <011> direction which lies in the bc plane which has a c-axis component, and therefore, information on the crystallite thickness can be obtained.

Therefore, the magnitude of the crystallite size in these two directions can provide information on the crystallite morphology through a shape factor defined as <110>/<011>. When the ratio is large, the crystals are large in the ab plane but thin in the bc plane, hence they are "plate-like", as the ratio approaches unity, both dimensions are similar and hence the crystallite morphology is more cuboidal or spherical in shape.

Table A provides X-ray diffraction data on all three samples studied. The degree of crystallinity was found not to change as a function of particle size, with the small particles having the same percent crystallinity as the much larger particles.

The crystallite size in the ab plane was observed to decrease monotonically as particle size increased in both samples. Conversely, the crystallite size in the bc plane (estimate of the c-axis component) was observed to increase monotonically as a function of particle size.

These results suggest that the crystallite shape is changing as a function of particle size. The crystallite shape in the small particles is more "plate-like" with the aspect ratio [<110>/<011>]≡2.5–3.5, as the particle grows the aspect ratio moves towards ≡1–1.5 suggesting a crystallite more cuboidal/spherical in shape. Thus the shape of the crystallite domains embedded in the granular resin changes from "plate-like" to cuboidal/spherical as the particles grow in size from PAN (<125 μm) to 10 mesh (>2000 μm). The particles could be viewed as having a graded type microstructure.

The observed behavior in this catalyst system is just one example of a graded microstructure. The opposite structure could form with cuboidal/spherical crystallites at the center which then transition over to a more "plate-like" morphology. An alternative crystallite morphology may be "rod-like" in which the shape factor becomes <1. The distribution of different crystallite morphologies could lead to a wide range of possible graded microstructures that could be controlled by the type of catalyst.

TABLE A

X-ray Diffraction Data from Example 13 Samples

| Sample | % Xal | % Para | % Am | FWHM (110) deg | FWHM (011)° | Xal Size (110)Å | Xal Size (011)Å |
|---|---|---|---|---|---|---|---|
| A | | | | | | | |
| 10 Mesh-1 | 55.8 | 4.3 | 39.9 | 0.4086 | 0.5883 | 197.7 | 143.4 |
| 10 Mesh-2 | 56.2 | 4.7 | 39.1 | 0.3926 | 0.5883 | 205.8 | 143.4 |
| 10 Mesh-3 | 56.1 | 5.3 | 38.6 | 0.4091 | 0.5883 | 197.5 | 143.4 |
| 60 Mesh-1 | 55.6 | 6.5 | 37.8 | 0.3557 | 0.6647 | 227.2 | 126.9 |
| PAN-1 | 53.7 | 3.9 | 42.4 | 0.3410 | 0.8433 | 230.2 | 100.0 |
| PAN-2 | 55.1 | 5.6 | 39.4 | 0.3450 | 0.7190 | 234.2 | 117.3 |
| Av. (10 Mesh) | 56.0 | 4.8 | 39.2 | 0.4034 | 0.5883 | 200.4 | 143.4 |
| Stdev (10) | 0.2 | 0.50 | 0.6 | 0.0094 | 0.0000 | 4.7 | 0.0 |
| Av. (60/Pan) | 54.8 | 5.3 | 39.9 | 0.3506 | 0.7423 | 230.5 | 114.7 |
| Stdev (60/Pan) | 1.0 | 1.3 | 2.3 | 0.0054 | 0.0916 | 3.5 | 13.6 |
| C | | | | | | | |
| 10 Mesh-1 | 61.9 | 4.1 | 34.0 | 0.3028 | 0.4678 | 266.9 | 180.3 |
| 10 Mesh-2 | 60.8 | 3.1 | 36.1 | 0.2975 | 0.4678 | 271.5 | 180.3 |
| 10 Mesh-3 | 60.0 | 3.3 | 36.7 | 0.2970 | 0.4695 | 272.1 | 179.6 |
| 60 Mesh-1 | 61.5 | 5.3 | 33.2 | 0.2672 | 0.5274 | 302.4 | 159.9 |
| PAN-1 | 59.3 | 3.8 | 36.9 | 0.2393 | 0.5477 | 337.7 | 154.0 |
| PAN-2 | 59.9 | 6.9 | 33.2 | 0.2517 | 0.5875 | 321.0 | 143.6 |
| Av. (10 Mesh) | 60.92 | 3.50 | 35.6 | 0.2991 | 0.4684 | 270.2 | 180.1 |
| Stdev (10) | 1.0 | 0.5 | 1.4 | 0.0032 | 0.0010 | 2.9 | 0.4 |
| Av. (60/Pan) | 60.2 | 5.3 | 34.4 | 0.2527 | 0.5542 | 320.4 | 152.5 |
| Stdev (60/Pan) | 1.1 | 1.5 | 2.1 | 0.0140 | 0.0306 | 17.6 | 8.3 |
| B | | | | | | | |
| 10 Mesh-1 | 63.4 | 7.9 | 28.6 | 0.2931 | 0.3638 | 275.9 | 229.2 |
| 10 Mesh-2 | 65.2 | 6.8 | 28.0 | 0.2278 | 0.3638 | 355.0 | 229.2 |
| 10 Mesh-3 | 63.6 | 6.8 | 29.7 | 0.2518 | 0.5895 | 321.2 | 143.3 |
| 60 Mesh-1 | 62.7 | 6.1 | 31.2 | 0.1800 | 0.6451 | 449.3 | 131.0 |
| PAN-1 | 64.7 | 6.7 | 28.6 | 0.1768 | 0.6451 | 457.4 | 131.0 |
| PAN-2 | 65.9 | 6.9 | 28.2 | 0.1754 | 0.6451 | 461.1 | 131.0 |
| Av. (10 Mesh) | 64.1 | 7.2 | 28.8 | 0.2576 | 0.4422 | 317.4 | 200.6 |
| Stdev (10) | 1.00 | 0.7 | 0.8 | 0.0330 | 0.1275 | 39.7 | 49.6 |
| Av. (60/Pan) | 64.1 | 6.6 | 29.3 | 0.1774 | 0.6451 | 455.9 | 131.0 |
| Stdev (60/Pan) | 1.2 | 0.4 | 1.6 | 0.0024 | 0.0000 | 6.0 | 0.0 |

For Tables B, C and D

CHMS is the high molecular weight species (over 500,000) CLMS is the low molecular weight species (less than 3000), VLD is very low density, LD is low density, HD is high density, CCLDI is crystallizable chain length distribution index and is defined in U.S. Pat. No. 5,798,427. CDI (50) is composition distribution index that measures how much polymer is within 25% of either side of the median. CDI (100) is composition distribution index that measures how much polymer is within 50% of either side of the median. Both composition distributions are measured using the Temperature Rising Elution Fractionation (TREF) technique as described in Wild et al (J. Polym. Sci. Phys. Ed. Vol 20, p441–445 (1982).) A dilute solution of the polymer in a solvent such as 1,2,4-trichlorobenzene is loaded into a packed column at high temperature. The column is allowed to cool slowly at 0.1° C./min. to ambient temperature. During the slow cooling process, the ethylene polymer is crystallized onto the packing in the order of increasing branching (decreasing crystallinity) with decreasing temperature. Once cooled, the column is reheated at 0.7° C./min, with a constant solvent flow through the column and the effluent is monitored with an infrared concentration detector. The CDI(100) and CDI(50) indices are similar to the "Composition Distribution Breadth Index" (CDBI). CDBI is defined as the weight percent of the copolymer chains having a comonomer content within 50% (±25%) of the median total molar comonomer content (see U.S. Pat. No. 5,470,811). The difference between the CDBI and the CDI (50) index is that the CDI(50) utilizes the mean branching frequency (or comonomer content) instead of the median comonomer content. The CDI(50) is determined from the TREF data by converting the elution temperature to branching frequency as follows:

Branching frequency can be expressed as the average distance (in $CH_2$ units) between branches along the main polymer chain backbone or as the crystallizable chain length (L) where, $$L \approx \frac{1000}{BF} \text{ and } \lim_{BF \to 0} L \to 2260$$

Utilizing moments of distribution analogous to the molecular weight distribution, one can define a number average ($L_n$) and weight average ($L_w$) moments for $L_i$ where:

$$L_n = 1/\Sigma_i(w_i/L_i) \text{ and } L_w = \Sigma_i w_i L_i$$

$w_i$ is the weight fraction of the polymer component i having an average backbone chain spacing $L_i$ between two adjacent branch points. The composition distribution index or crystallizable chain length distribution index (CCLDI) is then defined as:

$$CCLDI = L_w/L_n$$

The mean branching frequency is calculated by:

$$\overline{BF} = \sum_{i=1}^{\infty} W_i b_i$$

were $W_i$ and $b_i$ are the weight fraction and branch frequency respectively at each slice i of the TREF chromatogram. CDI(50) is then calculated by determining the accumulative weight fraction contained within ±25% of BF. CDI(100) is defined as the accumulative weight fraction contained within ±50% of BF.

TABLE B

Characterization data for polymer A

| Fraction | 1 | 4 | 5 | 6 |
|---|---|---|---|---|
| Mn | 10,604 | 8,320 | 8,815 | 8,831 |
| Mw | 230,395 | 227,935 | 234,524 | 247,901 |
| Mw/Mn | 19.2 | 27.4 | 26.6 | 28.1 |
| CHMS (%) | 11.3 | 13.1 | 13.7 | 14.5 |
| CLMS (%) | 1.3 | 2.2 | 2.0 | 2.0 |
| VLD (%) | 3.5 | 5.7 | 3.6 | 7 |
| LD (%) | 5.8 | 7.6 | 4.9 | 8.8 |
| HD (%) | 66.1 | 62 | 67.7 | 64.1 |
| CCLDI | 10.9 | 12.4 | 10.6 | 12.9 |
| CDI (50) (%) | 9.8 | 10.2 | 8.7 | 10 |
| CDI (100) (%) | 19.5 | 20.2 | 17.1 | 19.7 |

TABLE C

Characterization data for Polymer B

| Fraction | 1 | 3 | 4 | 5 | 6 |
|---|---|---|---|---|---|
| Mn | 12,335 | 11.486 | 10,957 | 10,408 | 10,400 |
| Mw | 285,402 | 263,008 | 249,496 | 244,990 | 248,000 |
| Mw/Mn | 23.1 | 22.9 | 22.8 | 23.5 | 23.8 |
| CHMS (%) | 17.1 | 15.9 | 15.3 | 15.0 | 15.2 |
| CLMS (%) | 0.5 | 0.6 | 0.7 | 0.7 | 0.73 |
| VLD (%) | 4.2 | 5.9 | 2.5 | 3.8 | 2.3 |
| LD (%) | 5.7 | 7.6 | 3.8 | 5.5 | 3.8 |
| HD (%) | 65.5 | 60.9 | 63.8 | 58 | 62.6 |
| CCLDI | 11 | 11.7 | 9.7 | 10.5 | 9.7 |
| CDI (50) (%) | 11 | 13.9 | 12.5 | 15.5 | 14.1 |
| CDI (100) (%) | 20.6 | 26.5 | 23.5 | 28.8 | 25.3 |

TABLE D

Characterization data for Polymer C

| Fraction | 1 | 4 | 5 | 6 |
|---|---|---|---|---|
| Mn | 13,114 | 13,081 | 11,451 | 11,328 |
| Mw | 243,241 | 236,908 | 219,370 | 217,120 |
| Mw/Mn | 18.5 | 18.2 | 19.2 | 19.2 |
| CHMS (%) | 13.7 | 13.6 | 12.6 | 12.5 |
| CLMS (%) | 0.7 | 0.6 | 0.9 | 1.0 |
| VLD (%) | 1.5 | 2.5 | 1.8 | 3.9 |
| LD (%) | 1.9 | 3.3 | 2.9 | 4.5 |
| HD (%) | 84.3 | 77 | 78.6 | 75.4 |
| CCLDI | 6.6 | 8.4 | 8.1 | 9.2 |
| CDI (50) (%) | 4.1 | 9.2 | 8.3 | 11.8 |
| CDI (100) (%) | 9.3 | 17.7 | 16.11 | 21.5 |

All documents described herein are incorporated by reference herein, including any priority documents and/or testing procedures. As is apparent form the foregoing general description and the specific embodiments, while forms of the invention have been illustrated and described, various modifications can be made without departing from the spirit and scope of the invention. Accordingly it is not intended that the invention be limited thereby.

What is claimed is:

1. Polyolefin having an Mw/Mn of 10 or more and wherein the melt indices of Fractions 1, 4 and 6 of the polyolefin do not vary by more than 20% relative to the mean of Fractions 1, 4 and 6 and wherein Fractions 1, 4 and 6 are obtained by using the following sieves:

| Sieve size | Fraction Collected | Fraction Name |
|---|---|---|
| 10 mesh | >2000 µm | Fraction 1 |
| 18 mesh | 2000–1000 µm | Fraction 2 |
| 35 mesh | <1000–500 µm | Fraction 3 |
| 60 mesh | <500–250 µm | Fraction 4 |
| 120 mesh | <250–125 µm | Fraction 5 |
| pan | <125 µm | Fraction 6. |

2. The polyolefin of claim 1 wherein the polyolefin is a homopolymer of ethylene.

3. The polyolefin of claim 1 wherein the polyolefin is a copolymer of ethylene and a C3 to C20 linear, branched or cyclic olefin.

4. The polyolefin of claim 1 wherein the polyolefin is a copolymer of ethylene and a C3 to C12 linear or branched alpha-olefin.

5. The polyolefin of claim 1 wherein the polyolefin is a copolymer of ethylene and a one or more of propylene, butene, hexene, pentene, heptene, octene, nonene, decene, 4-methyl-pentene-1, 3-methyl pentene-1, 3,5,5-trimethyl hexene-1, and dodecene.

6. The polyeolefin of claim 1 wherein the percent crystallinity of Fractions 1, 4 and 6 of the polyeolefin do not vary by more than 6% relative to the mean of Fractions 1, 4 and 6.

7. The polyolefin of claim 1 wherein the Mw/Mn of Fractions 1, 4 and 6 of the polyolefin do not vary by more than 20% relative to the mean of Fractions 1, 4 and 6.

8. The polyolefin of claim 1 wherein Fraction 1 has an aspect ratio of 0.5–1.5, fraction 4 has an aspect ratio of 1.2 to 4, and Fraction 6 has an aspect ratio of about 1.75 to 5 provided that the aspect ratios of the Fractions differ by at least 0.3.

9. The polyolefin of claim 1 wherein:

a) the percent crystallinity of Fractions 1, 4 and 6 of the polyolefin do not vary by more than 6% relative to the mean of Fractions 1, 4 and 6, b) the Mw/Mn of Fractions 1, 4 and 6 of the polyolefin do not vary by more than 20% relative to the mean of Fractions 1, 4 and 6, and c) Fraction 1 has an aspect ratio of 0.5–1.5, fraction 4 has an aspect ratio of 1.2 to 4, Fraction 6 has an aspect ratio of about 1.75 to 5 provided that the aspect ratios of the Fractions differ by at least 0.3.

10. Polyolefin wherein the percent crystallinity of Fractions 1, 4 and 6 of the polyolefin do not vary by more than 6% relative to the mean of Fractions 1, 4 and 6 and wherein Fractions 1, 4 and 6 are obtained by using the following sieves:

| Sieve size | Fraction Collected | Fraction Name |
| --- | --- | --- |
| 10 mesh | >2000 μm | Fraction 1 |
| 18 mesh | 2000–1000 μm | Fraction 2 |
| 35 mesh | <1000–500 μm | Fraction 3 |
| 60 mesh | <500–250 μm | Fraction 4 |
| 120 mesh | <250–125 μm | Fraction 5 |
| pan | <125 μm | Fraction 6. |

11. The polyolefin of claim 10 wherein the polyolefin is a homopolymer of ethylene.

12. The polyolefin of claim 10 wherein the polyolefin is a copolymer of ethylene and a C3 to C20 linear, branched or cyclic olefin.

13. The polyolefin of claim 10 wherein the polyolefin is a copolymer of ethylene and a C3 to C12 linear or branched alpha-olefin.

14. The polyolefin of claim 10 wherein the polyolefin is a copolymer of ethylene and a one or more of propylene, butene, hexene, pentene, heptene, octene, nonene, decene, 4-methyl-pentene-1, 3-methyl pentene-1, 3,5,5-trimethyl hexene-1, and dodecene.

15. The polyolefin of claim 10 wherein the Mw/Mn of Fractions 1, 4 and 6 of the polyolefin do not vary by more than 20% relative to the mean of Fractions 1, 4 and 6.

16. The polyolefin of claim 10 wherein Fraction 1 has an aspect ratio of 0.5–1.5, fraction 4 has an aspect ratio of 1.2 to 4, Fraction 6 has an aspect ratio of about 1.75 to 5 provided that the aspect ratios of the Fractions differ by at least 0.3.

17. The polyolefin of claim 10 wherein Fraction 1 has an aspect ratio of 0.5–1.5, fraction 4 has an aspect ratio of 1.2 to 4, Fraction 6 has an aspect ratio of about 1.75 to 5 provided that the aspect ratios of the Fractions differ by at least 0.5.

18. A film produced by blowing, extruding or casting the polyethylene of claim 14.

19. A molded article produced by blow molding or extrusion molding the polyethylene of claim 14.

20. Polyolefin having an Mw/Mn of 10 or more and wherein the Mw/Mn of Fractions 1, 4 and 6 of the polyolefin do not vary by more than 20% relative to the mean of Fractions 1, 4 and 6 and wherein Fractions 1, 4 and 6 are obtained by using the following sieves:

| Sieve size | Fraction Collected | Fraction Name |
| --- | --- | --- |
| 10 mesh | >2000 μm | Fraction 1 |
| 18 mesh | 2000–1000 μm | Fraction 2 |
| 35 mesh | <1000–500 μm | Fraction 3 |
| 60 mesh | <500–250 μm | Fraction 4 |
| 120 mesh | <250–125 μm | Fraction 5 |
| pan | <125 μm | Fraction 6. |

21. The polyolefin of claim 20 wherein the polyolefin is a homopolymer of ethylene.

22. The polyolefin of claim 20 wherein the polyolefin is a copolymer of ethylene and a C3 to C20 linear, branched or cyclic olefin.

23. The polyolefin of claim 20 wherein the polyolefin is a copolymer of ethylene and a C3 to C12 linear or branched alpha-olefin.

24. The polyolefin of claim 20 wherein the polyolefin is a copolymer of ethylene and a one or more of propylene, butene, hexene, pentene, heptene, octene, nonene, decene, 4-methyl-pentene-1, 3-methyl pentene-1, 3,5,5-trimethyl hexene-1, and dodecene.

25. The polyolefin of claim 20 wherein the percent crystallinity of Fractions 1, 4 and 6 of the polyolefin do not vary by more than 6% relative to the mean of Fractions 1, 4 and 6.

26. The polyolefin of claim 20 wherein Fraction 1 has an aspect ratio of 0.5–1.5, fraction 4 has an aspect ratio of 1.2 to 4, Fraction 6 has an aspect ratio of about 1.75 to 5 provided that the aspect ratios of the Fractions differ by at least 0.3.

27. A film produced by blowing, extruding or casting the polyethylene of claim 24.

28. A molded article produced by blow molding or extrusion molding the polyethylene of claim 24.

29. The polyolefin of claim 20 wherein the Mw/Mn is 20 or more.

30. Polyolefin wherein Fraction 1 has an aspect ratio of 0.5–1.5, fraction 4 has an aspect ratio of 1.2 to 4, Fraction 6 has an aspect ratio of about 1.75 to 5 provided that the aspect ratios of the Fractions differ by at least 0.3, and wherein Fractions 1, 4 and 6 are obtained by using the following sieves:

| Sieve size | Fraction Collected | Fraction Name |
| --- | --- | --- |
| 10 mesh | >2000 μm | Fraction 1 |
| 18 mesh | 2000–1000 μm | Fraction 2 |
| 35 mesh | <1000–500 μm | Fraction 3 |
| 60 mesh | <500–250 μm | Fraction 4 |
| 120 mesh | <250–125 μm | Fraction 5 |
| pan | <125 μm | Fraction 6. |

31. The polyolefin of claim 30 wherein the polyolefin is a homopolymer of ethylene.

32. The polyolefin of claim 30 wherein the polyolefin is a copolymer of ethylene and a C3 to C20 linear, branched or cyclic olefin.

33. The polyolefin of claim 30 wherein the polyolefin is a copolymer of ethylene and a C3 to C12 linear or branched alpha-olefin.

34. The polyolefin of claim 30 wherein the polyolefin is a copolymer of ethylene and a one or more of propylene, butene, hexene, pentene, heptene, octene, nonene, decene, 4-methyl-pentene-1, 3-methyl pentene-1, 3,5,5-trimethyl hexene-1, and dodecene.

35. The polyolefin of claim 30 wherein the percent crystallinity of Fractions 1, 4 and 6 of the polyolefin do not vary by more than 6% relative to the mean of Fractions 1, 4 and 6.

36. The polyolefin of claim 30 wherein the Mw/Mn of Fractions 1, 4 and 6 of the polyethylene do not vary by more than 20% relative to the mean of Fractions 1, 4 and 6.

37. The polyolefin of claim 30 wherein the aspect ratios differ by at least about 0.5.

38. The polyolefin of claim 30 wherein the aspect ratios differ by at least about 1.0.

39. The polyolefin of claim 30 wherein the aspect ratio of Fraction 1 is less than the aspect ration of Fraction 4 is less than the aspect ratio of Fraction 6.

40. The polyolefin of claim 30 wherein the polyolefin has a Mw/Mn of about 8 or more.

41. The polyolefin of claim 30 wherein the polyolefin has a density of 0.925 g/cm$^3$ or more.

42. A film produced by blowing, extruding or casting the polyolefin of claim 30.

43. A molded article produced by blow molding or extrusion molding the polyolefin of claim 30.

44. The polyolefin of claim 30 having an Mw/Mn of 15 or more.

45. A polyethylene wherein:
   A) the melt indices of Fractions 1, 4 and 6 of the polyethylene do not vary by more than 20% relative to the mean of Fractions 1, 4 and 6; and/or
   B) the percent crystallinity of Fractions 1, 4 and 6 of the polyethylene do not vary by more than 6% relative to the mean of Fractions 1, 4 and 6; and/or
   C) the Mw/Mn of Fractions 1, 4 and 6 of the polyethylene do not vary by more than 20% relative to the mean of Fractions 1, 4 and 6; and/or
   D) Fraction 1 has an aspect ratio of 0.5–1.5, fraction 4 has an aspect ratio of 1.2 to 4, Fraction 6 has an aspect ratio of about 1.75 to 5 provided that the aspect ratios of the Fractions differ by at least 0.3; and/or
   E) the polyethylene has an Mw/Mn of 10 or more;
and wherein Fractions 1, 4 and 6 are obtained by using the following sieves:

| Sieve size | Fraction Collected | Fraction Name |
|---|---|---|
| 10 mesh | >2000 μm | Fraction 1 |
| 18 mesh | 2000–1000 μm | Fraction 2 |
| 35 mesh | <1000–500 μm | Fraction 3 |
| 60 mesh | <500–250 μm | Fraction 4 |
| 120 mesh | <250–125 μm | Fraction 5 |
| pan | <125 μm | Fraction 6. |

46. The polyethylene of claim 45 wherein

A) the melt indices of Fractions 1, 4 and 6 of the polyethylene do not vary by more than 20% relative to the mean of Fractions 1, 4 and 6; and
   B) the percent crystallinity of Fractions 1, 4 and 6 of the polyethylene do not vary by more than 6% relative to the mean of Fractions 1, 4 and 6; and
   C) the Mw/Mn of Fractions 1, 4 and 6 of the polyethylene do not vary by more than 20% relative to the mean of Fractions 1, 4 and 6; and
   D) Fraction 1 has an aspect ratio of 0.5–1.5, fraction 4 has an aspect ratio of 1.2 to 4, Fraction 6 has an aspect ratio of about 1.75 to 5 provided that the aspect ratios of the Fractions differ by at least 0.3.

47. The polyethylene of claim 46 wherein the SEC graph has one positive slope, one negative slope, one inflection point and an Mw/Mn of 20 or more.

48. The polyethylene of claim 46 wherein the SEC graph has two or more positive slopes, two or more negative slopes, three or more inflection points and an Mw/Mn of 10 or more.

49. The polyethylene of claim 46 wherein the SEC graph has one or more positive slopes, one or more negative slopes, one or more inflection points, an Mw/Mn of 10 or more and a change in slope on any of the slopes of 20% or more as compared to the slop before the change.

* * * * *